(12) United States Patent
Hase et al.

(10) Patent No.: US 12,053,237 B2
(45) Date of Patent: Aug. 6, 2024

(54) CATHETER AND RECANALIZATION CATHETER SYSTEM

(71) Applicant: ASAHI INTECC CO., LTD., Seto (JP)

(72) Inventors: Yukiko Hase, Seto (JP); Osamu Katoh, Seto (JP); Yoshiki Kaneko, Seto (JP); Kazuya Kubo, Seto (JP); Ryotaro Kojima, Seto (JP); Maiko Kataoka, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 986 days.

(21) Appl. No.: 17/031,990

(22) Filed: Sep. 25, 2020

(65) Prior Publication Data

US 2021/0060293 A1    Mar. 4, 2021

Related U.S. Application Data

(63) Continuation of application No. PCT/JP2019/014182, filed on Mar. 29, 2019.
(Continued)

(51) Int. Cl.
*A61M 25/09* (2006.01)
*A61B 18/14* (2006.01)
(Continued)

(52) U.S. Cl.
CPC ..... *A61B 18/1492* (2013.01); *A61M 25/0071* (2013.01); *A61M 25/09* (2013.01);
(Continued)

(58) Field of Classification Search
CPC .......... A61B 2018/00077; A61B 2018/00214; A61B 2018/00577; A61B 2018/00982;
(Continued)

(56) References Cited

U.S. PATENT DOCUMENTS

| | | | | |
|---|---|---|---|---|
| 7,381,200 B2* | 6/2008 | Katoh | ............... | A61M 25/0084 604/93.01 |
| 2004/0116809 A1* | 6/2004 | Chow | ..................... | A61B 8/12 600/439 |

(Continued)

FOREIGN PATENT DOCUMENTS

| | | |
|---|---|---|
| CN | 101005870 A | 7/2007 |
| CN | 104161548 A | 11/2014 |

(Continued)

*Primary Examiner* — Nathan R Price
*Assistant Examiner* — Haden Matthew Ritchie
(74) *Attorney, Agent, or Firm* — Oliff PLC

(57) ABSTRACT

A catheter includes a shaft having a first lumen inside thereof, an expansion/contraction portion that is disposed on a distal end portion of the shaft and is expandable and contractible in a radial direction, and an actuation portion that expands and contracts the expansion/contraction portion. The expansion/contraction portion has a fixed portion fixed to the shaft, a sliding portion capable of sliding in a longitudinal direction of the shaft on an outer peripheral face of the shaft, and a suspension portion extending in the longitudinal direction of the shaft that connects the fixed portion with the sliding portion. When the sliding portion is slid toward the fixed portion by the actuation portion, the suspension portion expands in a radial direction of the shaft.

3 Claims, 28 Drawing Sheets

Related U.S. Application Data

(60) Provisional application No. 62/650,149, filed on Mar. 29, 2018.

(51) Int. Cl.
*A61M 25/00* (2006.01)
*A61B 18/00* (2006.01)

(52) U.S. Cl.
CPC ............... *A61B 2018/00077* (2013.01); *A61B 2018/00214* (2013.01); *A61B 2018/00577* (2013.01); *A61B 2018/00982* (2013.01); *A61B 2018/1467* (2013.01); *A61M 2025/09008* (2013.01); *A61M 2205/3327* (2013.01)

(58) Field of Classification Search
CPC .. A61B 2018/1467; A61B 2018/00285; A61B 2018/00583; A61B 18/1492; A61B 18/042; A61B 8/12; A61B 8/445; A61B 6/12; A61B 2017/22095; A61M 25/0071; A61M 25/09; A61M 2025/09008; A61M 2025/3327; A61M 2025/0197; A61M 2025/1056; A61M 2025/0183
See application file for complete search history.

(56) References Cited

U.S. PATENT DOCUMENTS

| | | | |
|---|---|---|---|
| 2004/0186368 A1 | 9/2004 | Ramzipoor et al. | |
| 2006/0106375 A1 | 5/2006 | Werneth et al. | |
| 2006/0122591 A1* | 6/2006 | Keidar .................... | A61B 8/12 606/41 |
| 2012/0053485 A1 | 3/2012 | Bloom | |
| 2012/0053565 A1* | 3/2012 | Lee ........................ | A61M 25/10 604/510 |
| 2013/0072957 A1* | 3/2013 | Anderson ...... | A61B 17/320758 606/191 |
| 2014/0200603 A1* | 7/2014 | Zhou .................. | A61B 17/3207 606/185 |
| 2014/0309533 A1 | 10/2014 | Yamashita et al. | |
| 2015/0196730 A1 | 7/2015 | O'Callaghan et al. | |
| 2015/0257779 A1* | 9/2015 | Sinelnikov .............. | A61N 7/022 606/28 |
| 2016/0045714 A1 | 2/2016 | Zhou et al. | |
| 2022/0265152 A1* | 8/2022 | McCaffrey .......... | A61B 5/6852 |

FOREIGN PATENT DOCUMENTS

| | | |
|---|---|---|
| EP | 3 057 545 A1 | 8/2016 |
| JP | H05-507219 A | 10/1993 |
| JP | 2001-518328 A | 10/2001 |
| JP | 2002-538881 A | 11/2002 |
| JP | 2007-532265 A | 11/2007 |
| JP | 5564416 B2 | 7/2014 |
| JP | 2014-526347 A | 10/2014 |
| JP | 2016-516473 A | 6/2016 |
| JP | 6030655 B2 | 11/2016 |
| JP | 6118335 B2 | 4/2017 |
| JP | 6182660 B2 | 8/2017 |
| WO | 91/17710 A1 | 11/1991 |
| WO | 99/16499 A1 | 4/1999 |
| WO | 00/50115 A2 | 8/2000 |
| WO | 00/54683 A1 | 9/2000 |
| WO | 2005/102440 A2 | 11/2005 |
| WO | 2008/120209 A1 | 10/2008 |
| WO | 2013/043592 A1 | 3/2013 |
| WO | 2013/086271 A1 | 6/2013 |
| WO | 2013/111700 A1 | 8/2013 |
| WO | 2014/150424 A1 | 9/2014 |
| WO | 2015/058096 A1 | 4/2015 |

* cited by examiner

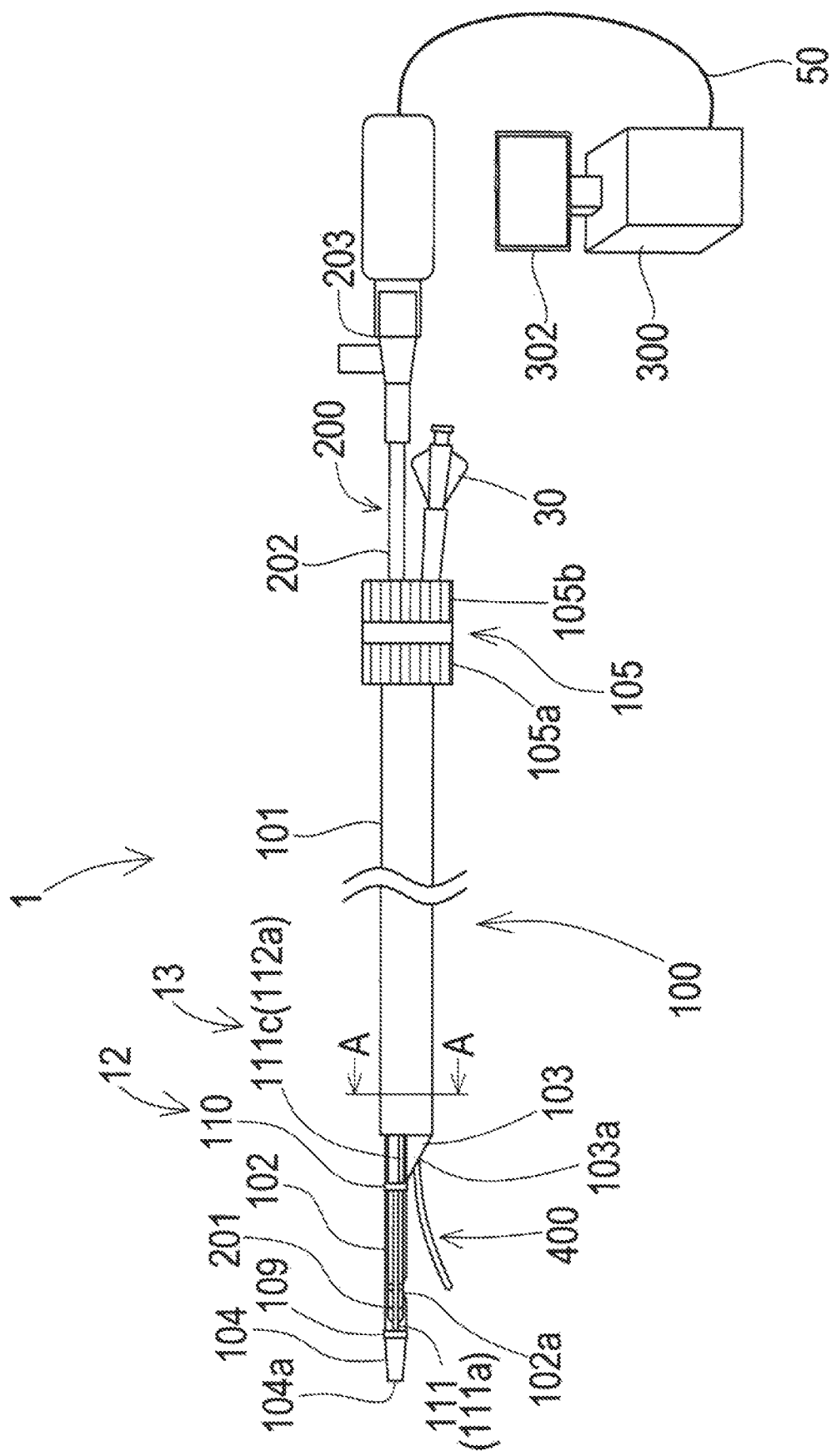

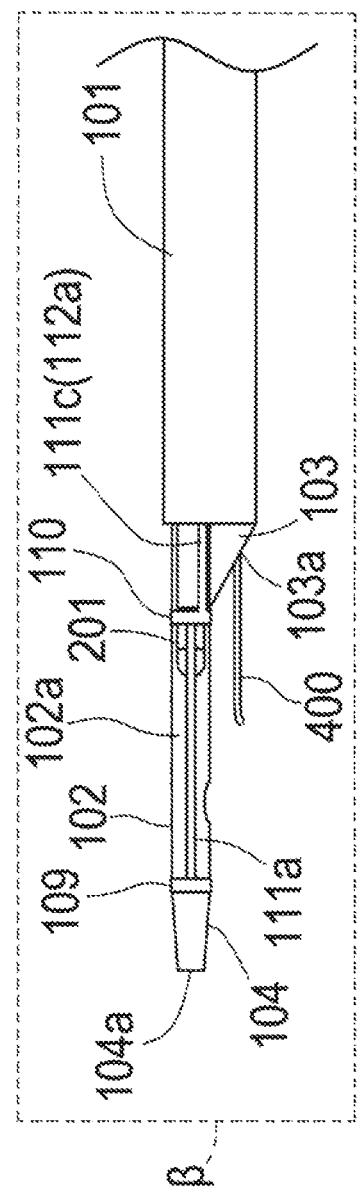

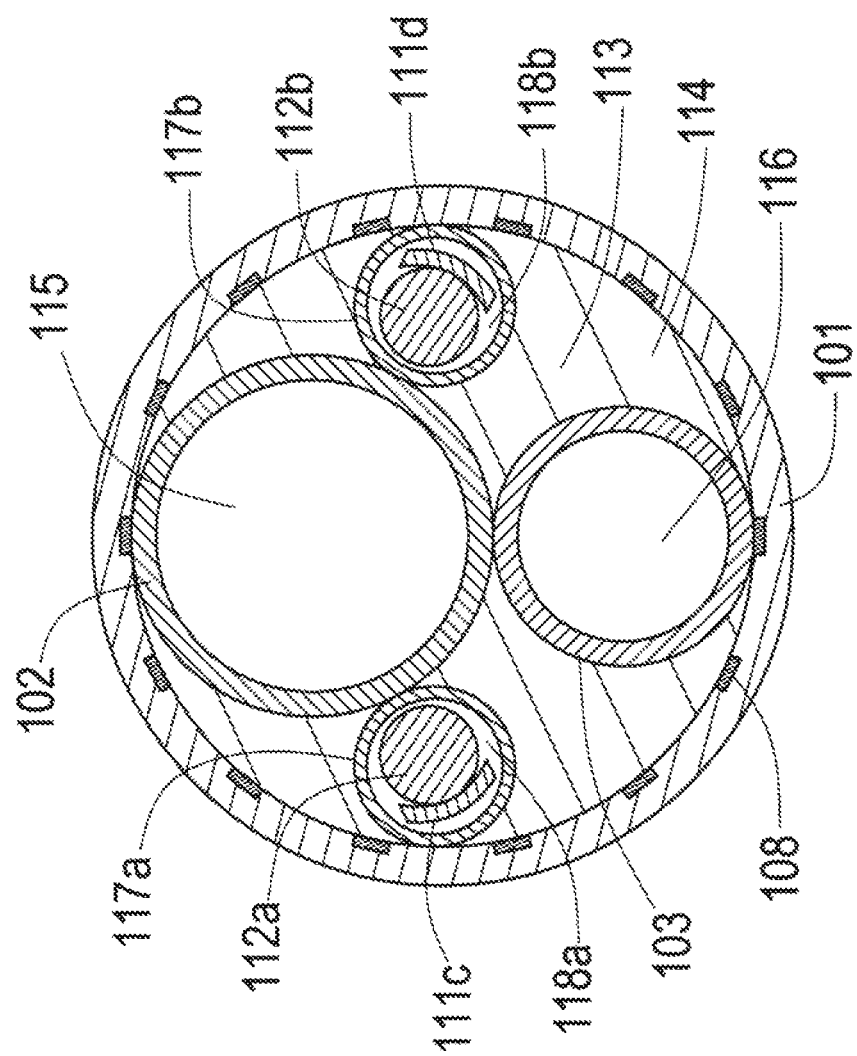

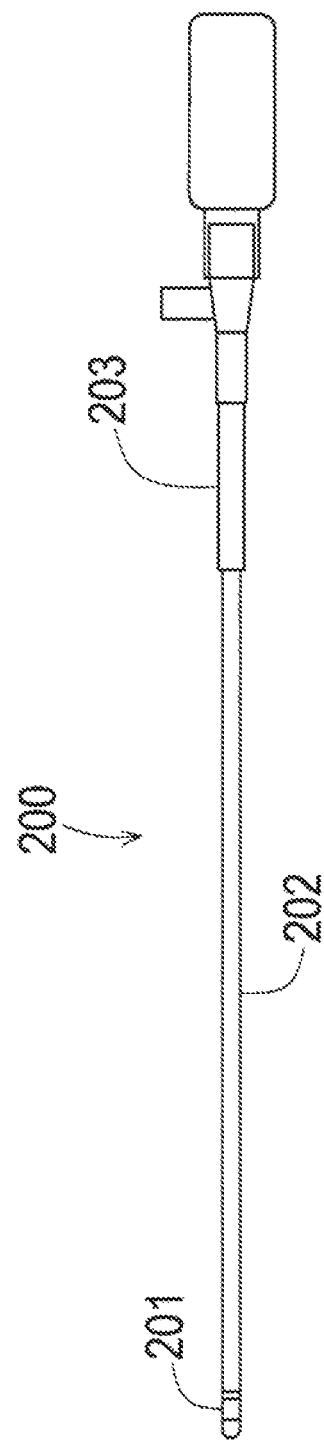

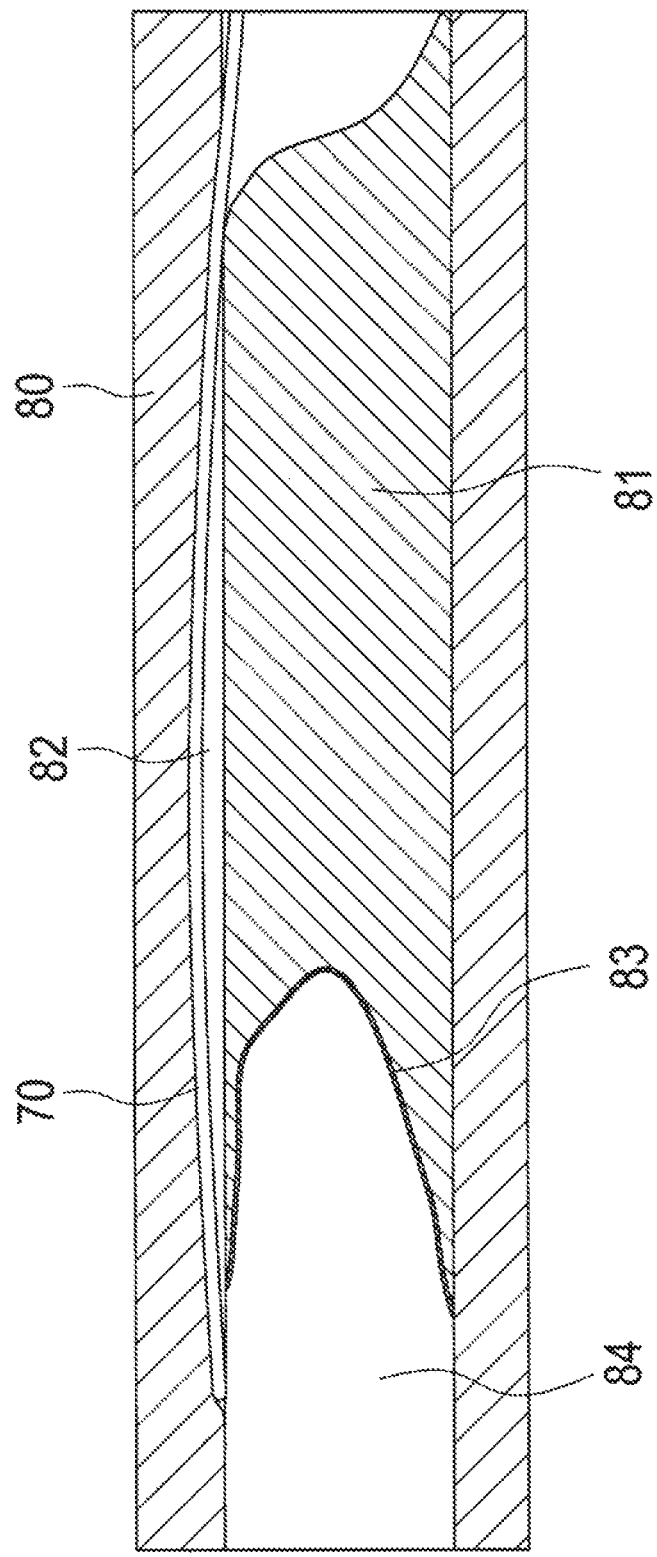

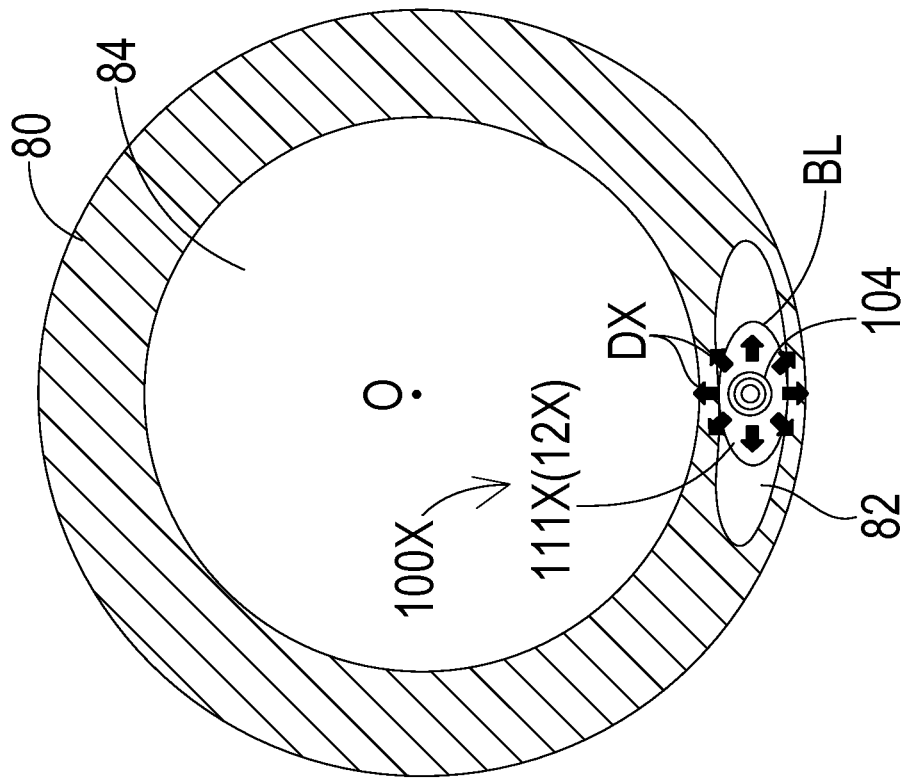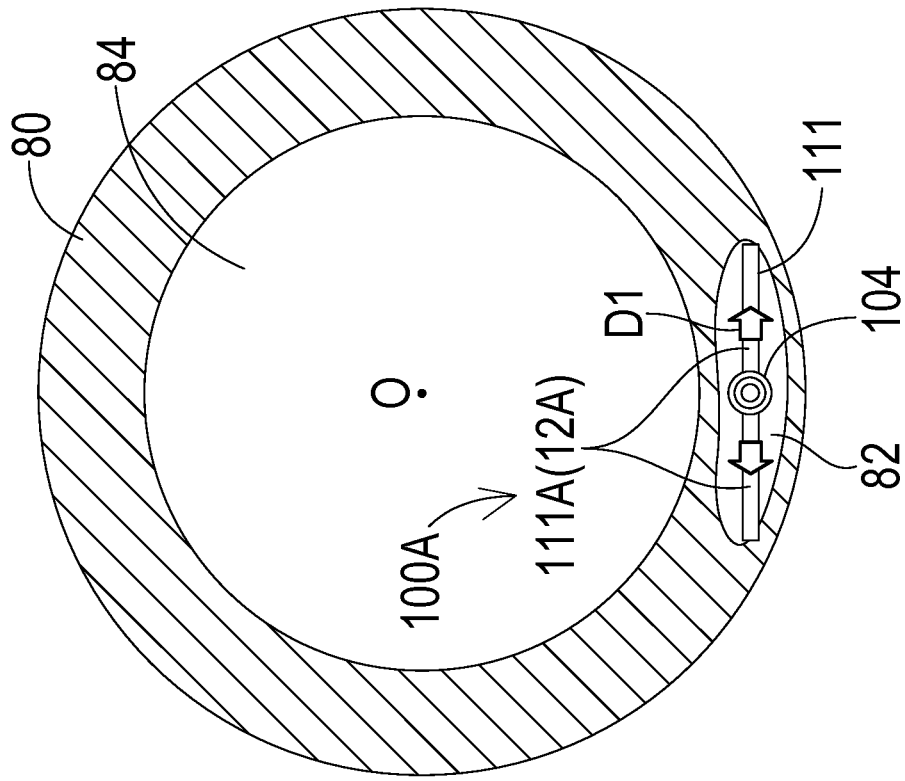

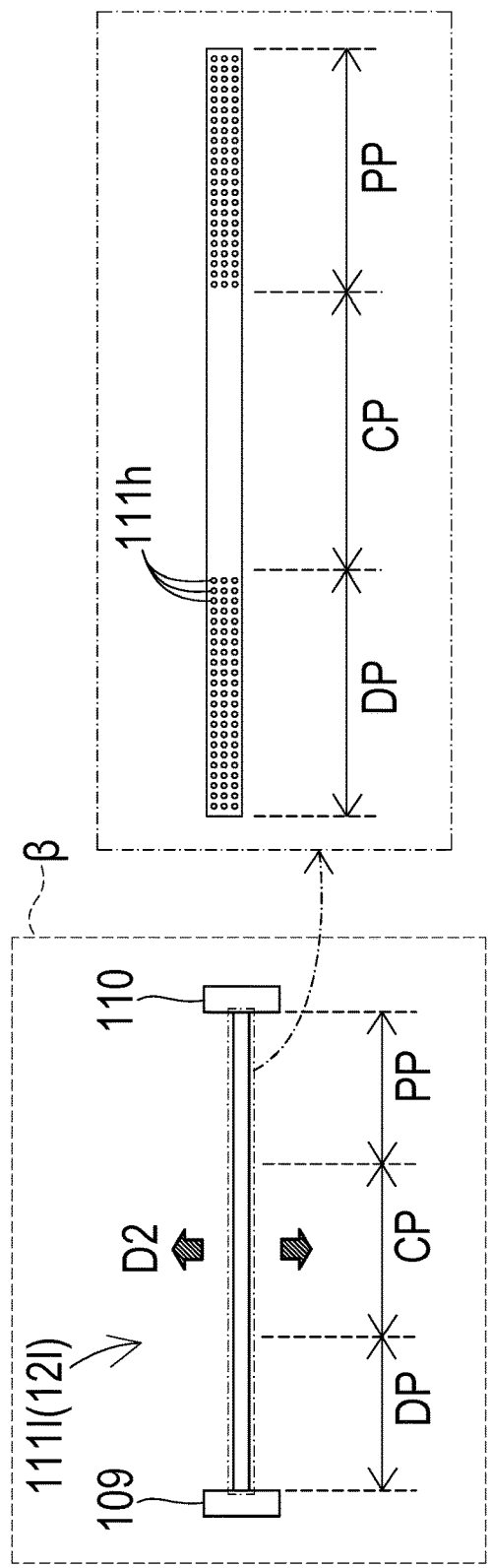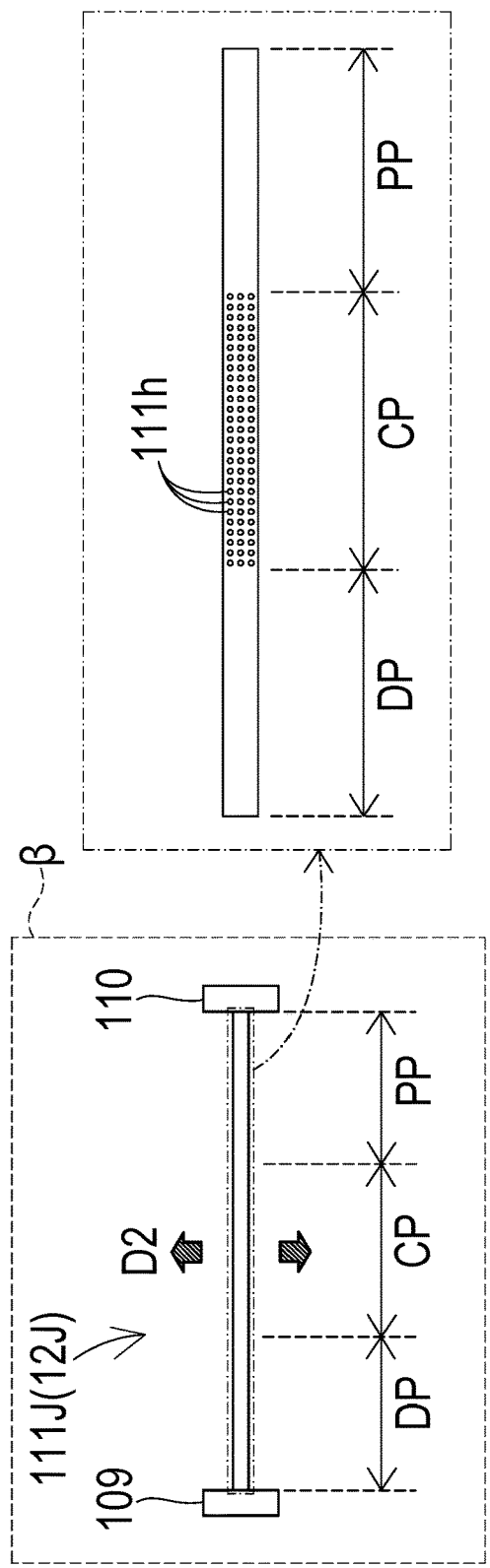

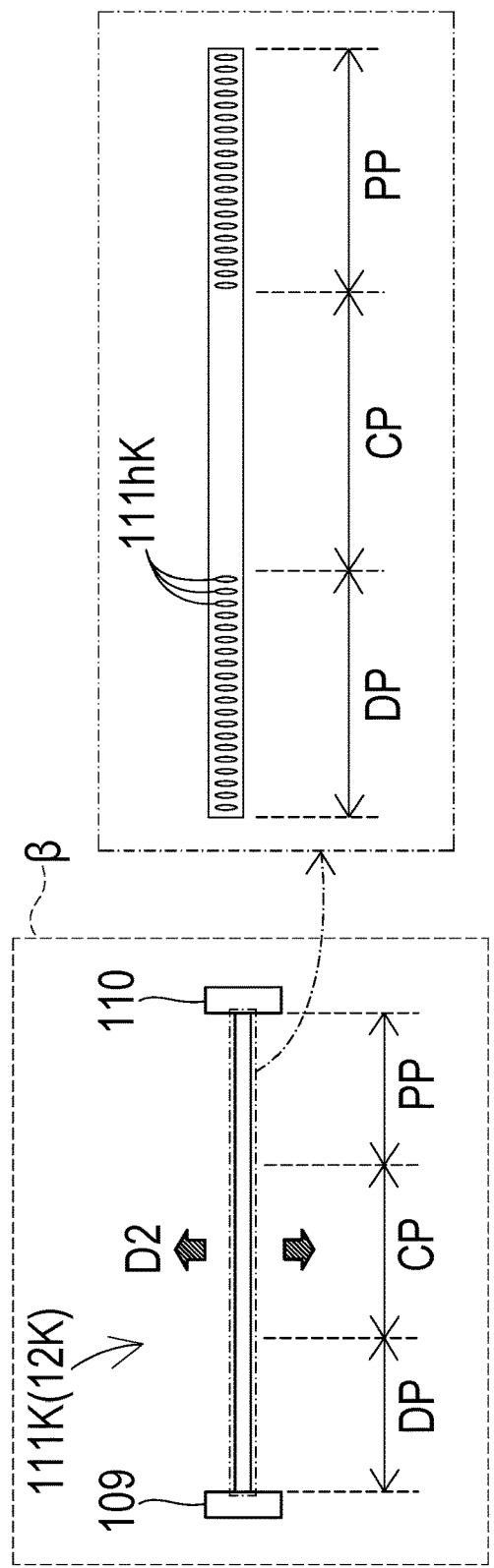
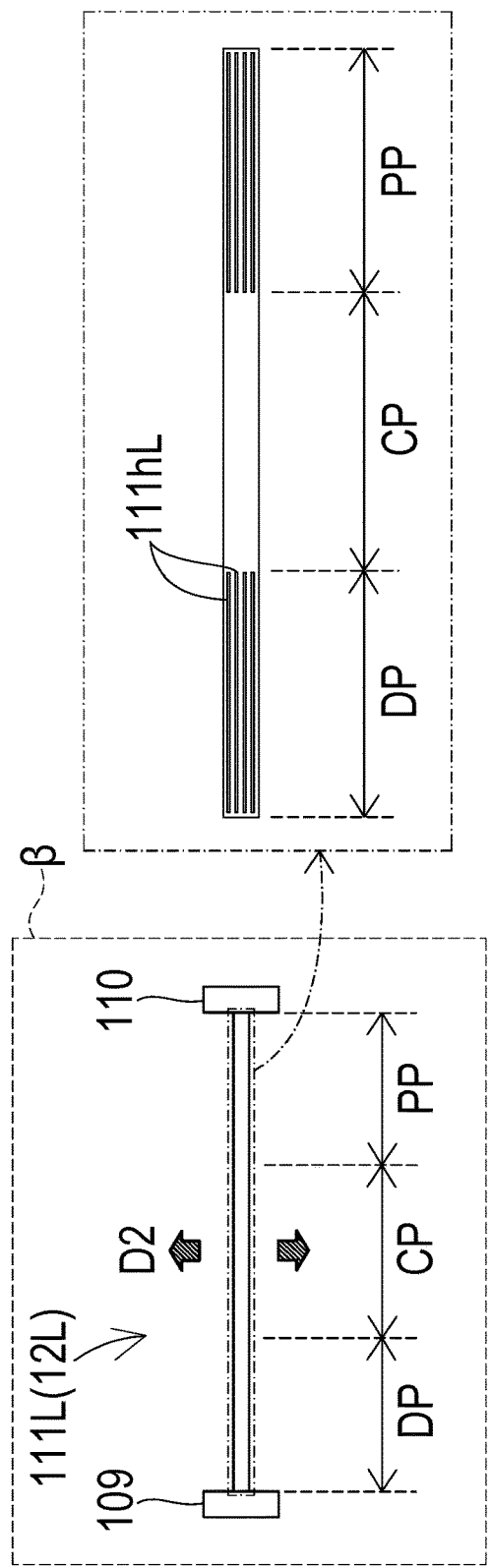
Fig. 13A
Fig. 13B

CATHETER AND RECANALIZATION CATHETER SYSTEM

CROSS REFERENCE TO RELATED APPLICATIONS

This is a Continuation of Application No. PCT/JP2019/014182 filed Mar. 29, 2019, which claims the benefit of U.S. Provisional Application No. 62/650,149 filed Mar. 29, 2018. The disclosure of the prior applications is hereby incorporated by reference herein in its entirety.

BACKGROUND

The disclosed embodiments relate to a catheter.

In some cases, such as chronic total occlusion (CTO), a blood vessel may be occluded by an obstruction. Japanese Patent Publication Nos. 5564416, 6030655, 6118335, and 6182660 disclose a subintimal approach in which a guide wire is reinserted into a true cavity from a false cavity for CTO canalization (revascularization). Herein, the false cavity refers to any dissected lumen other than true cavities formed of guide wires. Also, Japanese Patent Publication Nos. 5564416, 6030655, 6118335, and 6182660 disclose a configuration in which a catheter or a catheter assembly usable for such a subintimal approach includes a balloon for fixing the catheter in a false cavity.

SUMMARY

Herein, the false cavity is a dissociated cavity formed by a partially exfoliated vascular tissue e.g. between an inner membrane tissue layer and an outer membrane tissue layer, and therefore the false cavity has a cross-sectional shape flatter than the true cavity. On the other hand, the balloon has a substantially circular cross-sectional shape. Thus, the technologies described in Japanese Patent Publication Nos. 5564416, 6030655, 6118335, and 6182660 have had a problem that expansion of a balloon in a false cavity is likely to expand the false cavity.

Note that such a problem is not limited to canalization of CTO, and is common to all cases of fixing a catheter in a false cavity. In addition, such a problem is not limited to vascular systems, and is common to all devices that are inserted into a living body lumen, such as a lymphatic system, a biliary system, a urinary system, a respiratory system, a digestive system, a secretory gland, and a genital organ.

The disclosed embodiments have been devised to address at least a part of the aforementioned problems, and an object of the disclosed embodiments is to provide a catheter that can be fixed inside a false cavity by a method different from the conventional method. This can be achieved according to the following aspects.

(1) According to an aspect of the disclosed embodiments, a catheter is provided. This catheter includes a shaft having a first lumen inside thereof, an expansion/contraction portion that is disposed on a distal end portion of the shaft and is expandable and contractible in a radial direction, and an actuation portion that expands and contracts the expansion/contraction portion. The expansion/contraction portion includes a fixed portion fixed to the shaft, a sliding portion capable of sliding in a longitudinal direction of the shaft on an outer peripheral face of the shaft, and a suspension portion extending in the longitudinal direction of the shaft that connects the fixed portion with the sliding portion. When the sliding portion is slid toward the direction of the fixed portion by the actuation portion, the suspension portion expands in a radial direction of the shaft.

According to this configuration, when the sliding portion is slid toward the direction of the fixed portion by the actuation portion, the suspension portion expands in the radial direction of the shaft, so that the catheter can be fixed inside a false cavity. In addition, the suspension portion connects the fixed portion fixed to the shaft with the sliding portion slidable on the outer peripheral face of the shaft and has a shape extending in the longitudinal direction of the shaft, and therefore the suspension portion has a different configuration from the conventional configuration (expandable and contractible tubular balloon). As a result, the configuration makes it possible to provide a catheter that can be fixed inside the false cavity by a method different from the conventional method.

(2) In the catheter according to the aforementioned aspect, the suspension portion includes a distal end portion positioned on the distal end side, a proximal end portion positioned on the proximal end side, and a central portion positioned between the distal end portion and the proximal end portion, in the longitudinal direction. The central portion of the suspension portion may have a rigidity different from rigidities of the distal end portion and the proximal end portion.

According to this configuration, in the suspension portion, the rigidity of the central portion is relatively different from the rigidities of the distal end portion and the proximal end portion positioned on both ends of the central portion, and therefore a contact area where the suspension portion is in contact with a living tissue can be increased compared to a case without the difference in rigidity. Thus, a risk of enlarging the false cavity (dissociated cavity) due to expansion of the suspension portion can be reduced, and furthermore injury of the living body due to the suspension portion when turning the catheter in the circumferential direction can be suppressed. Also, since a friction resistance with a living tissue wall face can be enhanced as the contact area increases, the operation of moving the catheter in the longitudinal direction, and a resistance force against the operation of moving the catheter in the longitudinal direction and the operation of turning the catheter in the circumferential direction can be enhanced. In other words, a force to fix the catheter can be enhanced.

(3) In the catheter according to the aforementioned aspect, the central portion of the suspension portion may have a thickness different from thicknesses of the distal end portion and the proximal end portion.

According to this configuration, in the suspension portion, the thickness of the central portion is made relatively different from the thicknesses of the distal end portion and the proximal end portion, so that they can have different rigidities. In addition, a resistance force against torsion during the operation of turning in the circumferential direction can be enhanced by varying the rigidity depending on the thickness (wall thickness).

(4) In the catheter according to the aforementioned aspect, the suspension portion may have holes formed either in the central portion or in the distal and proximal end portions.

According to this configuration, in the suspension portion, the holes are formed on either the central portion or the distal and proximal end portions, so that they can have different rigidities. In addition, a resistance force against torsion during the operation of turning in the circumferential direction can be enhanced by varying the rigidity depending on the presence or absence of the holes.

(5) In the catheter according to the aforementioned aspect, the central portion of the suspension portion may have a width different from widths of the distal end portion and the proximal end portion.

According to this configuration, in the suspension portion, the width of the central portion is made relatively different from the widths of the distal end portion and the proximal end portion, so that they can have different rigidities. In addition, a structure that the suspension portion is easily laser-processed can be obtained by varying the rigidity depending on the width.

(6) In the catheter according to the aforementioned aspect, in the suspension portion, the distal end portion and the proximal end portion are substantially identical in length in the longitudinal direction, and the central portion of the suspension portion may be longer than the distal end portion in the longitudinal direction.

According to this configuration, in the suspension portion, the length of the distal end portion and the length of the proximal end portion are substantially the same in the longitudinal direction, and the length of the central portion is larger than the length of the distal end portion, so that the contact area where the suspension portion is in contact with the living tissue can be increased, and a fixation force for the catheter can be further enhanced. As a result, for example, even when not only a sensor for acquiring information on the living tissue but also a medical device requiring a backup force such as a penetration guide wire for penetrating the living tissue are used while inserted into the catheter, the catheter can be fixed inside the false cavity, and deviation of the catheter can be suppressed.

(7) In the catheter according to the aforementioned aspect, the suspension portion may expand a boundary between the central portion and the distal end portion and a boundary between the central portion and the proximal end portion are each bent, and, when the suspension portion expands, the central portion moves away from the outer peripheral face of the shaft substantially parallel to the longitudinal direction so as to expand substantially trapezoidally.

According to this configuration, a shape of the expanded suspension portion can be substantially trapezoid such that each of the boundary between the central portion and the distal end portion and the boundary between the central portion and the proximal end portion is bent. Thus, a risk of enlarging the false cavity due to expansion of the suspension portion can be further reduced, and injury of the living tissue due to the suspension portion can be further suppressed. In addition, the resistance force against the operation of moving the catheter in the longitudinal direction and the operation of turning the catheter in the circumferential direction can be further enhanced, and the fixation force for the catheter can be further enhanced.

(8) In the catheter according to the aforementioned aspect, the suspension portion may have a cross-sectional shape obtained by curving a rectangular shape to make the rectangular shape protrude outward in the radial direction of the shaft.

According to this configuration, since the cross-sectional shape of the suspension portion is a shape obtained by curving a rectangular shape so as to protrude outward in the radial direction of the shaft, hooking of the suspension portion can be suppressed by slidingly moving a distal end face of the protrusion on the living tissue when the catheter is turned in the circumferential direction, and injury of the living tissue due to the suspension portion can be suppressed.

(9) In the catheter according to the aforementioned aspect, the suspension portion includes a first suspension portion and a second suspension portion, and the first suspension portion and the second suspension portion may be arranged opposite to each other.

According to this configuration, since the suspension portion includes two suspension portions (first suspension portion and second suspension portion), the resistance force against the operation of moving the catheter in the longitudinal direction and the operation of turning the catheter in the circumferential direction can be further enhanced, and the fixation force for the catheter can be further enhanced. In addition, the first suspension portion and the second suspension portion are arranged so as to be opposite to each other, and individually expand in the radial direction of the shaft, and thereby the shape of the expanded suspension portion (expansion/contraction portion) can be made to fit the shape of the false cavity having a flat cross-sectional shape.

(10) In the catheter according to the aforementioned aspect, a first opening allowing the first lumen to communicate with an outside may be formed in a position on the shaft where a second virtual plane perpendicular to a first virtual plane including the first suspension portion and the second suspension portion, the second virtual plane being located between the fixed portion and the sliding portion, intersects with the outer peripheral face of the shaft, when the first suspension portion and the second suspension portion expand in the radial direction.

According to this configuration, the shaft has the first opening for communicating between the first lumen and the outside, at a position where the second virtual plane perpendicular to the first virtual plane and positioned between the fixed portion and the sliding portion intersects with the outer peripheral face of the shaft. The catheter can also be used as a rapid exchange-type catheter by protruding the proximal end side of a delivery guide wire from this first opening, and therefore diversity of the procedure can be widened and usability can be improved.

(11) In the catheter according to the aforementioned aspect, the shaft may further include a second lumen extending from a proximal end toward a distal end of the shaft that is juxtaposed with the first lumen and is shorter than the first lumen in the longitudinal direction of the shaft, and an end face, in which a second opening allowing the distal end portion of the second lumen to communicate with an outside is formed.

According to this configuration, since the shaft further includes the second lumen juxtaposed with the first lumen, a plurality of medical devices can be simultaneously held in one catheter, e.g. an IVUS as a sensor for acquiring information on the living tissue is inserted into the first lumen, and the penetration guide wire for penetrating the living tissue is inserted into the second lumen. In addition, among the first lumen and the second lumen extending from the proximal end to the distal end of the shaft, the second lumen is shorter than the first lumen. Thus, the IVUS is inserted into the longer first lumen, and a transducer (site that transmits and receives ultrasonic waves to/from the living tissue) of the IVUS is disposed on the distal end portion of the first lumen, so that the distal end portion of the medical device (e.g. delivery guide wire, penetration guide wire, or the like) inserted into the shorter second lumen can be observed with the IVUS. Thereby, an operator can recognize a condition inside the living body lumen (e.g. CTO) and a position of the distal end portion of the medical device (e.g. delivery guide wire, penetration guide wire, or the like) in real time only by a two-dimensional image from the IVUS. That means, the catheter having this configuration makes it possible to achieve a procedure of the sensor under a guide without requiring a skill for separately manipulating a plurality of devices in a blood vessel, and a skill for three-dimensionally reconstructing sensor images and X-ray images, that have been conventionally required for the procedures of the sensor under the guide (e.g. IVUS Guide). Furthermore, since the catheter having this configuration makes it possible to achieve the procedure only by confirming the image from the sensor, a number of acquisitions of the X-ray images can also be decreased, and it can be expected that an exposure dose to an operator and a patient associated with X-ray photography is decreased, and an amount of a contrast medium used for the X-ray photography is decreased.

In addition, according to this configuration, the shaft includes an end face having a second opening communicating between the distal end portion of the second lumen and the outside. Thereby, for example, the proximal end portion of the delivery guide wire is taken out from the first opening, and then the proximal end portion of the delivery guide wire is inserted into the second lumen from the second opening, so that the delivery guide wire can be fixed to the distal end portion of the shaft. Thus, by fixation of the delivery guide wire, the delivery guide wire can be oriented constantly in a certain direction on the image from the sensor, and, as a result, the operator can control the catheter such that the position of the target site relative to the catheter, where the penetration guide wire penetrates the living tissue, is optimized (optimum angle), by advancing/retracting and turning the catheter relative to the delivery guide wire while confirming the image from the sensor. Furthermore, in the catheter having this configuration, for the purpose of fixing the delivery guide wire, the distal end portion of the first lumen for the sensor is used. In other words, the first lumen is shared by the delivery guide wire and the sensor. Thus, the catheter can be reduced in diameter, and can be easily inserted into the living body lumen (e.g. into the coronary artery, the CTO, or the like), compared to a case of disposing a separate lumen for fixing the delivery guide wire. Furthermore, when the penetration guide wire penetrates the living tissue, the distal end portion of the penetration guide wire is protruded outward from the second opening while the penetration guide wire is inserted into the second lumen, so that the distal end portion of the penetration guide wire can confront the target site while obtaining the backup force.

(12) According to an aspect of the disclosed embodiments, a recanalization catheter system is provided. This recanalization catheter includes the catheter according to the aforementioned aspect having the first and second lumens. The first lumen includes a sensor for acquiring information on the living tissue, and a guide wire can be inserted into the second lumen, led to the outside through the second opening, and made to penetrate the living tissue.

Note that the disclosed embodiments can be achieved in various aspects. For example, the disclosed embodiments include a catheter, a method for manufacturing or using the catheter, a catheter system including the catheter and other devices such as a sensor, a delivery guide wire, and a penetration guide wire, a method for manufacturing or using the catheter system, or the like.

BRIEF DESCRIPTION OF DRAWINGS

FIG. 1 is a schematic diagram illustrating an overall configuration of a recanalization catheter system.

FIG. 2A is a schematic side view of a distal end portion of the catheter.

FIG. 3 is a schematic sectional view of the catheter taken along line A-A in FIG. 1.

FIG. 4 is a schematic diagram illustrating an imaging sensor.

FIG. 5A is a diagram illustrating a state in which a delivery guide wire is inserted into a coronary artery.

FIGS. 8A and 8B are explanatory diagrams illustrating a state of the expansion/contraction portion in a false cavity.

FIGS. 12A and 12B are explanatory diagrams illustrating configurations of an expansion/contraction portion according to a fifth aspect of the disclosed embodiments.

FIGS. 13A and 13B are explanatory diagrams illustrating other configurations of the expansion/contraction portion according to the fifth aspect of the disclosed embodiments.

DETAILED DESCRIPTION OF EMBODIMENTS

A. First Aspect

Figure 2B:
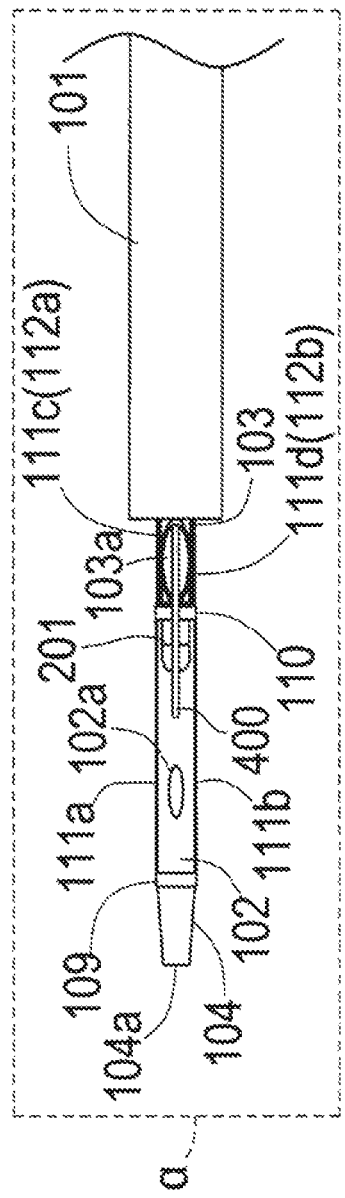
FIG. 2B is a schematic bottom view of the distal end portion of the catheter.
Figure 2C:
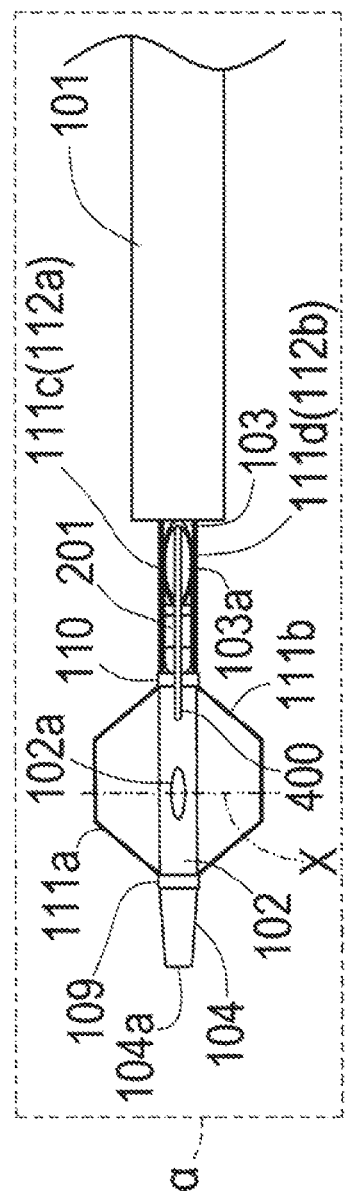
FIG. 2C is a schematic bottom view of the distal end portion of the catheter.

FIG. 1 is a schematic diagram illustrating an overall configuration of a recanalization catheter system 1. FIGS. 2A-2C are schematic diagrams illustrating a distal end portion of a catheter 100. FIG. 3 is a schematic sectional view of the catheter 100 taken along line A-A in FIG. 1. The recanalization catheter system 1 is used e.g. when treating CTO (chronic total occlusion) with an antegrade approach. The recanalization catheter system 1 includes the catheter 100, an imaging sensor 200, an imaging console 300, and a penetration guide wire 400. FIG. 1 shows a schematic side view of the catheter 100.

For the convenience of explanation, FIG. 1 includes a part where each component is illustrated in a relative ratio of a size different from the actual size. Also, FIG. 1 includes a part where a part of each component is exaggeratedly illustrated. Additionally, in FIG. 1, the left side is referred to as "distal end side" of each component, and the right side is referred to as proximal end side" of each component. Additionally, in each component, an end portion positioned on the distal end side is referred to as "distal end", and an end portion positioned on the proximal end side is referred to as "proximal end". Also, parts positioned on the distal end and in the vicinity of the distal end are referred to as "distal end portion", and parts positioned on the proximal end and in the vicinity of the proximal end are referred to as "proximal end portion". These definitions also apply to the following figures.

The catheter 100 includes a hollow outer shaft 101, a hollow first inner shaft 102, a hollow second inner shaft 103, and a hollow distal tip 104 continuous with the first inner shaft 102. The outer shaft 101, the first inner shaft 102, and the second inner shaft 103 have a long shape, and have substantially circular cross sections. The distal tip 104 has a tapered shape whose outer diameter gradually decreases toward the distal end, and has a substantially circular cross section.

A braid 108 (see FIG. 3) as a reinforcing member formed by braiding a wire is embedded inside the outer peripheral face of the outer shaft 101. The wire constituting the braid 108 may be made of a metal material, e.g. a stainless steel such as SUS304, a nickel-titanium alloy, an alloy including gold, platinum, or tungsten that are X-ray impermeable material, or the like. The wire constituting the braid 108 may be made of a known metal material other than the aforementioned materials. Incidentally, inside the outer peripheral face of the outer shaft 101, a hollow coil body (not illustrated) formed by winding a wire can be embedded instead of the braid 108. Like the braid 108, the wire constituting the hollow coil body may be made of a metal material, e.g. a stainless steel such as SUS304, a nickel-titanium alloy, an alloy including gold, platinum, or tungsten that are X-ray impermeable material, and the like. In addition, the wire constituting the hollow coil body may be made of a known metal material other than the aforementioned materials.

As illustrated in FIG. 3, the first inner shaft 102 and the second inner shaft 103 are inserted into an outer lumen 113 of the outer shaft 101. In addition, a hollow first wire shaft 117*a* and a hollow second wire shaft 117*b* are inserted into the outer lumen 113. The first inner shaft 102, the second inner shaft 103, the first wire shaft 117*a*, and the second wire shaft 117*b* extend substantially parallel to each other along a longitudinal direction of the outer shaft 101. In addition, the inside of the outer lumen 113 of the outer shaft 101 is sealed by a sealing member 114. The sealing member 114 is disposed between an inner peripheral face of the outer shaft 101 and outer peripheral faces of the first inner shaft 102, the second inner shaft 103, the first wire shaft 117*a*, and the second wire shaft 117*b*.

An imaging sensor 200 is inserted into a first inner lumen 115 of the first inner shaft 102 (not illustrated in FIG. 3). Hereinafter, the first inner lumen 115 is also simply referred to as "first lumen 115". The penetration guide wire 400 and a normal delivery guide wire (delivery guide wire 70 described below) are inserted into a second inner lumen 116 of the second inner shaft 103 (not illustrated in FIG. 3). Hereinafter, the second inner lumen 116 is also simply referred to as "second lumen 116". As described above, since the first inner shaft 102 forming the first lumen 115 and the second inner shaft 103 forming the second lumen 116 extend substantially parallel to each other, the first lumen 115 and the second lumen 116 are juxtaposed with each other (see FIG. 3).

As illustrated in FIG. 3, a first wire 112*a* and a second wire 112*b* described below are inserted into a first wire lumen 118*a* of the first wire shaft 117*a* and a second wire lumen 118*b* of the second wire shaft 117*b* respectively. In a state that the first wire 112*a* and the second wire 112*b* are connected to a first wire piece 111*c* and a second wire piece 111*d* respectively described below, the first wire 112*a* and the second wire 112*b* are inserted into the first wire lumen 118*a* and the second wire lumen 118*b* respectively. The first wire piece 111*c* and the second wire piece 111*d*, and the first wire 112*a* and the second wire 112*b* functionally act as an "actuation portion 13" for expanding and contracting a suspension portion 111 as an expansion/contraction portion 12.

As illustrated in FIG. 1, a regulator 105 for opening/closing the suspension portion 111, and advancing/retracting the imaging sensor 200 in the first lumen 115 described below is attached to the proximal end of the outer shaft 101. The regulator 105 includes a first dial 105*a* and a second dial 105*b* that can be individually operated. The first dial 105*a* is used for opening and closing the suspension portion 111, and the second dial 105*b* is used for advancing and retracting the imaging sensor 200. Details will be described below.

The first inner shaft 102 and the second inner shaft 103 protrudes from the distal end of the outer shaft 101. A part of the second inner shaft 103 protruding from the distal end of the outer shaft 101 is configured to be shorter than a part of the first inner shaft 102 protruding from the distal end of the outer shaft 101. That means, a length of the second lumen 116 in the second inner shaft 103 in the longitudinal direction is shorter than a length of the first lumen 115 in the first inner shaft 102 in the longitudinal direction. In addition, the distal end of the second inner shaft 103 slopes toward the first inner shaft 102.

An opening 103*a* communicating with the second lumen 116 of the second inner shaft 103 (see FIG. 3) is formed on the distal end of the second inner shaft 103. The opening 103a corresponds to the "second opening" that communicates between the distal end portion of the second lumen 116 and the outside. On the outer peripheral face of the first inner shaft 102, an opening 102a communicating with the first lumen 115 of the first inner shaft 102 (see FIG. 3) is formed between the distal end of the outer shaft 101 and the distal end of the first inner shaft 102. The opening 102a corresponds to the "first opening" that communicates between the distal end portion of the first lumen 115 and the outside.

The distal tip 104 is joined to the distal end of the first inner shaft 102. An opening 104a is formed on the distal end of the distal tip 104, and the opening 104a communicates with a lumen (not illustrated) inside the distal tip 104 and the first lumen 115 of the first inner shaft 102. The delivery guide wire 70 (see FIG. 5A) is inserted into the lumen inside the distal tip 104, the first lumen 115 of the first inner shaft 102, and the second lumen 116 of the second inner shaft 103. That means, the proximal end of the delivery guide wire 70 enters the inside of the catheter 100 (lumen inside the distal tip 104, and the first lumen 115) from the opening 104a, then once goes out of the catheter 100 from the opening 102a, again enters the second lumen 116 of the second inner shaft 103 from the opening 103a, passes through the second lumen 116, and goes out of the catheter 100 from the proximal end of the second inner shaft 103.

Incidentally, on the proximal end side of the opening 103a, a third opening (not illustrated) that penetrates the second inner shaft 103 and communicates with the second lumen 116 can be formed on the outer peripheral face of the outer shaft 101. In this case, the proximal end of the delivery guide wire 70 can be configured to go out of the catheter 100 from the third opening. In addition, another opening (not illustrated) may be formed instead of the opening 102a on the outer peripheral face of the first inner shaft 102. Specifically, another opening may be formed in a radial direction of the first inner shaft 102, at a position opposite to the opening 102a i.e. on the opposite side of the second inner shaft 103. In this case, the proximal end of the delivery guide wire 70 may enter the opening 104a, pass through the lumen inside the distal tip 104 and the first lumen 115 of the first inner shaft 102, and go out of the other opening.

The outer shaft 101, the first wire shaft 117a (see FIG. 3), the second wire shaft 117b (see FIG. 3), the sealing member 114 (see FIG. 3), the first inner shaft 102, the second inner shaft 103, and the distal tip 104 may be made of an insulating resin, e.g. an polyolefin such as polyethylene, polypropylene, and ethylene-propylene copolymer, a polyester such as polyethylene terephthalate, a thermoplastic resin such as polyvinyl chloride, ethylene-vinyl acetate copolymer, crosslinkable ethylene-vinyl acetate copolymer, and polyurethane, a polyamide elastomer, a polyolefin elastomer, a polyurethane elastomer, a silicone rubber, a latex rubber, or the like. Also, the outer shaft 101, the first wire shaft 117a, the second wire shaft 117b, the sealing member 114, the first inner shaft 102, the second inner shaft 103, and the distal tip 104 may be made of a known material other than the aforementioned materials.

In the first lumen 115 of a part of the first inner shaft 102 protruding from the distal end of the outer shaft 101, i.e. a part positioned from the distal end of the first inner shaft 102 to the distal end of the outer shaft 101, a transducer 201 and a driving cable 202 of the imaging sensor 200 described below are disposed. The transducer 201 transmits an ultrasonic wave to a living tissue through the first inner shaft 102 and receives a reflected sound of the ultrasonic wave. The imaging console 300 acquires an image of the living tissue based on difference between the sounds transmitted and received by the transducer 201. Thus, a part positioned from the distal end of the first inner shaft 102 to the distal end of the outer shaft 101 is preferably made of a resin having a smaller difference in an acoustic impedance from the living tissue compared to the part of the first inner shaft 102 positioned inside the outer shaft 101, e.g. polyethylene. The part from the distal end of the first inner shaft 102 to the distal end of the outer shaft 101 may be formed such that a thickness of an outer peripheral wall of the part is smaller than a thickness of an outer peripheral wall of the part of the first inner shaft 102 positioned inside the outer shaft 101.

The distal tip 104 is disposed on the distal end of the catheter 100, and is preferably made of a resin more flexible than the outer shaft 101, the first inner shaft 102, and the second inner shaft 103, e.g. a polyurethane elastomer for avoiding injury of the living tissue in the body cavity. The distal tip 104 can be joined to the first inner shaft 102 by any method, and e.g. joining with an insulating adhesive such as an epoxy adhesive can be adopted.

FIG. 2A is a schematic side view of the distal end portion of the catheter 100, and FIG. 2B and FIG. 2C are schematic bottom views of the distal end portion of the catheter 100. As illustrated in FIG. 2A, on the distal end portion of the catheter 100, the "expansion/contraction portion 12" composed of a fixed portion 109, a sliding portion 110, and the suspension portion 111 is attached to the outer peripheral face of the first inner shaft 102 exposed from the outer shaft 101. FIG. 2B illustrates a state that the suspension portion 111 is closed (contracted expansion/contraction portion 12), and FIG. 2C illustrates a state that the suspension portion 111 is opened (expanded expansion/contraction portion 12).

The fixed portion 109 is ring-shaped, and joined to the distal end of the first inner shaft 102 so as to be fixed to the first inner shaft 102. Incidentally, the fixed portion 109 may be joined to the proximal end of the distal tip 104, or may be joined to both the distal end of the first inner shaft 102 and the proximal end of the distal tip 104. The joining between the fixed portion 109 and the distal end of the first inner shaft 102, the joining between the fixed portion 109 and the proximal end of the distal tip 104, or the joining between the fixed portion 109 and both the distal end of the first inner shaft 102 and the proximal end of the distal tip 104 can be achieved by any method. For example, joining with an insulating adhesive such as an epoxy adhesive. Incidentally, the fixed portion 109 may be disposed closer to the proximal end side than the distal end side of the first inner shaft 102. The sliding portion 110 is ring-shaped, disposed apart from the fixed portion 109 on the proximal end side of the fixed portion 109, and slidably mounted along the longitudinal direction of the first inner shaft 102 on the outer peripheral face of the first inner shaft 102.

The suspension portion 111 is disposed between the fixed portion 109 and the sliding portion 110. The suspension portion 111 according to the first aspect of the disclosed embodiments includes a first suspension portion 111a and a second suspension portion 111b (the second suspension portion 111b is not illustrated in FIG. 1). The distal end and the proximal end of the first suspension portion 111a are joined to the fixed portion 109 and the sliding portion 110 respectively. Similarly, the distal end and the proximal end of the second suspension portion 111b are also joined to the fixed portion 109 and the sliding portion 110 respectively. Each of the first suspension portion 111a and the second suspension portion 111b connects the fixed portion 109 with the sliding portion 110, and extends in the longitudinal direction of the first inner shaft 102.

The first suspension portion 111a and the second suspension portion 111b are arranged so as to be opposite to each other in the radial direction of the first inner shaft 102. The first suspension portion 111a and the second suspension portion 111b are disposed so as to be present on a virtual plane α, as illustrated in FIG. 2B and FIG. 2C. As illustrated in FIG. 2A, the first inner shaft 102 and the second inner shaft 103 are disposed such that the longitudinal axis of the first inner shaft 102 and the longitudinal axis of the second inner shaft 103 are present in a virtual plane β. The first suspension portion 111a and the second suspension portion 111b are preferably arranged such that the virtual plane α and the virtual plane β are substantially perpendicular to each other. Incidentally, the virtual plane α including the first suspension portion 111a and the second suspension portion 111b is also referred to as a "first virtual plane".

Additionally, in a state that the first suspension portion 111a and the second suspension portion 111b are expanded (FIG. 2C), the opening 102a as the first opening is perpendicular to the virtual plane α including the first suspension portion 111a and the second suspension portion 111b, and is formed at a position where a virtual plane X positioned between the fixed portion 109 and the sliding portion 110 intersects with the outer peripheral face of the first inner shaft 102. In such a way, when the catheter 100 is positioned relative to a target site by advancing the catheter 100 along the delivery guide wire 70, an image of the delivery guide wire 70 acquired by the imaging sensor 200 can functionally act as a land mark. In addition, on the outer peripheral face of the first inner shaft 102, the opening 102a is disposed on the same side as of the second inner shaft 103 and the opening 103a and on the extended line of the second inner shaft 103 and the opening 103a. In such a way, the proximal end of the delivery guide wire 70 protruding from the opening 102a can be easily inserted into the second lumen 116 from the opening 103a. Incidentally, the virtual plane X perpendicular to the virtual plane a and positioned between the fixed portion 109 and the sliding portion 110 is also referred to as "second virtual plane".

As illustrated in FIG. 2B, when the first suspension portion 111a and the second suspension portion 111b are closed, the first suspension portion 111a and the second suspension portion 111b extend between the fixed portion 109 and the sliding portion 110, in the longitudinal direction of the first inner shaft 102, substantially parallel to the first inner shaft 102. When the first suspension portion 111a and the second suspension portion 111b are closed, the sliding portion 110 is disposed as close as possible to the proximal end side i.e. the opening 103a. The proximal end of the sliding portion 110 may be disposed at the distal end of the opening 103a. Thereby, lengths of the first suspension portion 111a and the second suspension portion 111b can be increased, and therefore, for example, deviation of the catheter 100 in a false cavity can be further reduced. In addition, as illustrated in FIG. 2C, when the sliding portion 110 moves toward the distal end of the first inner shaft 102, the first suspension portion 111a and the second suspension portion 111b expand outward in the radial direction of the first inner shaft 102, and open. In both states of the opened and closed suspension portion 111, the sliding portion 110 is disposed on the proximal end side of the opening 102a.

Cross-sectional shapes of the first suspension portion 111a and the second suspension portion 111b can be made rectangular. Thereby, the suspension portions can be easily expanded outward in the radial direction e.g. compared to the case that the cross-sectional shape is square or circle.

The suspension portion 111, the fixed portion 109, and the sliding portion 110 are made of a metal material or a resin material. When made of a metal material, they may be made of e.g. a stainless steel such as SUS304, a nickel-titanium alloy, an alloy including gold, platinum, or tungsten that are a X-ray impermeable material, and the like. When made of a resin material, they may be made of e.g. a polyolefin such as polyethylene, polypropylene, and ethylene-propylene copolymer, a polyester such as polyethylene terephthalate, a thermoplastic resin such as polyvinyl chloride, ethylene-vinyl acetate copolymer, crosslinkable ethylene-vinyl acetate copolymer, and polyurethane, a polyamide elastomer, a polyolefin elastomer, a polyurethane elastomer, a silicone rubber, a latex rubber, or the like. The suspension portion 111, the fixed portion 109, and the sliding portion 110 may be made of a known metal material or resin material other than the aforementioned materials. When the suspension portion 111 is made of a shape-memory nickel-titanium alloy, preferably a state in which the suspension portion 111 is closed is previously memorized to the nickel-titanium alloy. Thereby, the suspension portion 111 can be relatively easily transitioned from the open state to the closed state.

The suspension portion 111 can be joined to the fixed portion 109 and the sliding portion 110 by any method. When the suspension portion 111, the fixed portion 109, and the sliding portion 110 are made of a resin, or when the suspension portion 111 is made of a metal material and the fixed portion 109 and the sliding portion 110 are made of a resin material, or when the suspension portion 111 is made of a resin material and the fixed portion 109 and the sliding portion 110 are made of a metal material, joining with an adhesive e.g. an epoxy adhesive can be adopted. When the suspension portion 111, the fixed portion 109, and the sliding portion 110 are made of a metal material, it is possible to adopt joining by laser welding, or brazing using a metal solder such as silver solder, gold solder, zinc, Sn—Ag alloy, and Au—Sn alloy.

As illustrated in FIG. 2A to FIG. 2C, the sliding portion 110 is joined to the first wire 112a and the second wire 112b (only the first wire 112a is illustrated in FIG. 2A). Specifically, the first wire piece 111c described below is disposed on the proximal end of the sliding portion 110 (see FIG. 2E). The first wire 112a is arranged along the longitudinal direction of the first inner shaft 102 so as to overlap with this first wire piece 111c (see FIG. 2E and FIG. 3) and joined to the first wire piece 111c. Similarly, the second wire piece 111d described below is disposed on the proximal end of the sliding portion 110 (see FIG. 2E). The second wire 112b is disposed along the longitudinal direction of the first inner shaft 102 so as to overlap with this second wire piece 111d (see FIG. 2E and FIG. 3) and joined to the second wire piece 111d. Each of the first wire piece 111c and the second wire piece 111d passes through the first wire lumen 118a and the second wire lumen 118b described below and extends to the way to the outer shaft 101. The first wire 112a and the second wire 112b extend from the proximal end of the sliding portion 110 toward the proximal end of the first inner shaft 102 in the longitudinal direction of the first inner shaft 102 along the outer peripheral face of the middle part of the first inner shaft 102.

The first wire 112a is configured to be longer than the first wire piece 111c, but they may have the same length. Similarly, the second wire 112b is configured to be longer than the second wire piece 111d, but they may have the same length. As illustrated in FIG. 3, the first wire piece 111c and the second wire piece 111d are made of a thin plate member whose cross section is substantially rectangular or arcuate. The first wire 112a and the second wire 112b are made of a round wire having a substantially circular cross section. The first wire 112a is formed such that an outer diameter of a part overlapping with the first wire piece 111c is smaller than an outer diameter of a part not overlapping with the first wire piece 111c. Similarly, the second wire 112b is formed such that an outer diameter of a part overlapping with the second wire piece 111d is smaller than an outer diameter of a part not overlapping with the second wire piece 111d.

As illustrated in FIG. 2A, the first wire 112a and the first wire piece 111c are arranged substantially parallel to the closed first suspension portion 111a. In addition, the first wire 112a and the first wire piece 111c are deviated toward the second inner shaft 103 relative to the first suspension portion 111a in a circumferential direction of the sliding portion 110 (in other words, in a circumferential direction of the first inner shaft 102). Similarly, the second wire 112b and the second wire piece 111d are arranged substantially parallel to the closed second suspension portion 111b (not illustrated in FIG. 2A). In addition, the second wire 112b and the second wire piece 111d are arranged on the second inner shaft 103 side relative to the second suspension portion 111b in the circumferential direction of the sliding portion 110 (in other words, in the circumferential direction of the first inner shaft 102) (not illustrated in FIG. 2A).

As illustrated in FIG. 3, each of the first wire 112a and the second wire 112b is connected to the first dial 105a of the regulator 105 (see FIG. 1) through the first wire lumen 118a or the second wire lumen 118b respectively of the outer shaft 101. By operation of the first dial 105a, through the first wire 112a and the second wire 112b, the sliding portion 110 is moved toward the distal end of the first inner shaft 102 on the outer peripheral face of the first inner shaft 102, and thereby the suspension portion 111 can be expanded. At the same time, in order to expand the suspension portion 111 to an optimum size, a degree of expansion of the suspension portion 111 can be regulated while observing an image of a living tissue based on ultrasonic signals from the imaging sensor 200 described below by an imaging console 300 described below, so that vascular injury can be minimized. In addition, by another operation of the first dial 105a, the sliding portion 110 is moved toward the proximal end of the first inner shaft 102 through the first wire 112a and the second wire 112b on the outer peripheral face of the first inner shaft 102 in a state that the suspension portion 111 is expanded, so that the suspension portion 111 can be returned to the closed state.

The first wire 112a and the second wire 112b are made of a metal material or a resin material. When made of a metal material, they may be made of e.g. a chrome-molybdenum steel, a nickel-chrome-molybdenum steel, a stainless steel such as SUS304, a nickel-titanium alloy, or the like. When made of a resin material, they may be made of e.g. a super engineering plastic such as polyetheretherketone, polyetherimide, polyamideimide, polysulfone, polyimide, and polyethersulfone. The first wire 112a and the second wire 112b may be made of a known metal material or resin material other than these materials.

Figure 2D:
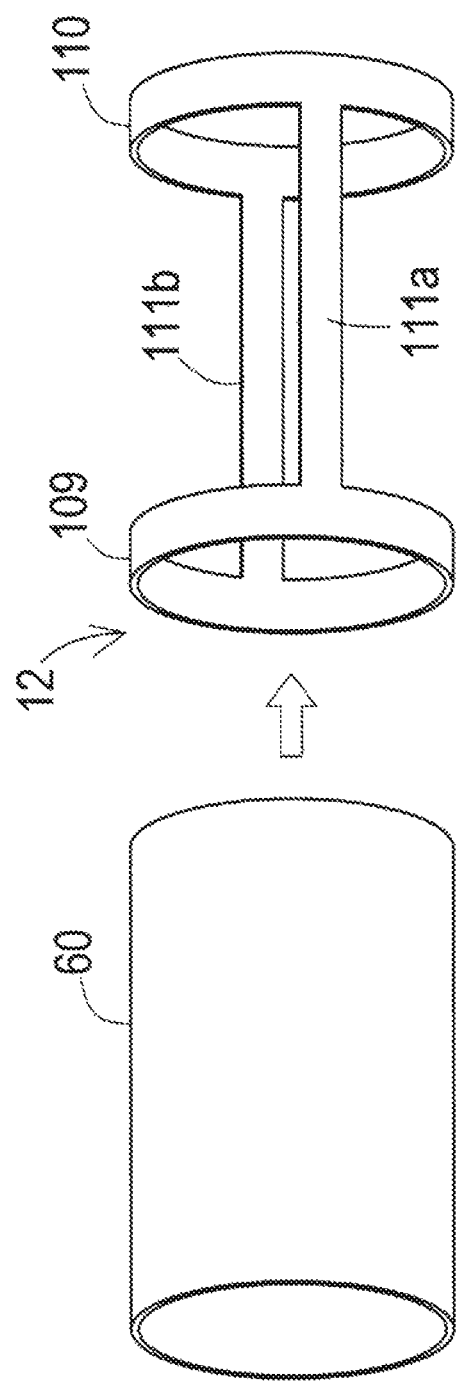
FIG. 2D is a diagram for explaining a method for integrally forming an expansion/contraction portion.

FIG. 2D is a diagram for explaining a method for integrally forming the expansion/contraction portion 12. Although the suspension portion 111, the fixed portion 109, and the sliding portion 110 as the expansion/contraction portion 12 may be formed as separate bodies, they can be integrally formed. When formed integrally, the fixed portion 109, the sliding portion 110, the first suspension portion 111a, and the second suspension portion 111b are formed by cutting out a side wall of a cylindrical hollow pipe 60 made of a resin material or a metal material, as illustrated in FIG. 2D. In the case of FIG. 2D, the first wire 112a and the second wire 112b are directly joined to the sliding portion 110.

In this case, the first wire 112a and the second wire 112b can be joined with the sliding portion 110 by any method. When the first wire 112a, the second wire 112b, and the sliding portion 110 are made of a resin, or when the first wire 112a and the second wire 112b are made of a metal material and the sliding portion 110 is made of a resin material, or when the first wire 112a and the second wire 112b are made of a resin material and the sliding portion 110 is made of a metal material, joining e.g. with an adhesive such as an epoxy adhesive can be adopted. When the first wire 112a, the second wire 112b, and the sliding portion 110 are made of a metal material, joining by laser welding, or brazing using a metal solder such as silver solder, gold solder, zinc, Sn—Ag alloy, and Au—Sn alloy can be adopted.

Figure 2E:
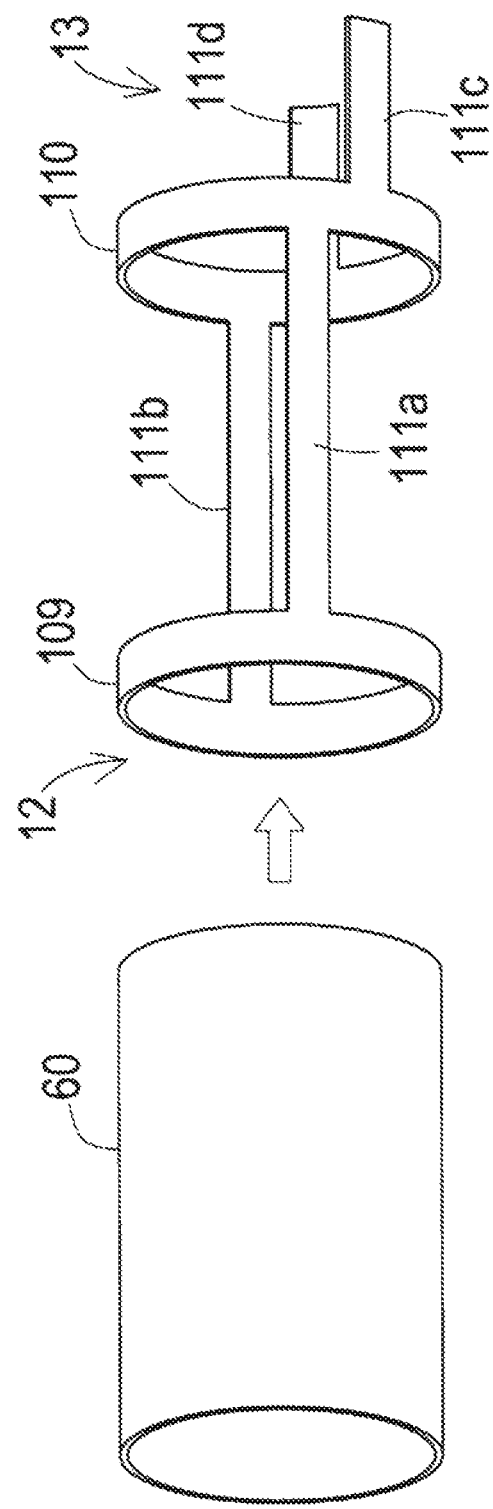
FIG. 2E is a diagram for illustrating a method for integrally forming the expansion/contraction portion and a part of an actuation portion.

FIG. 2E is a diagram for illustrating a method for integrally forming the expansion/contraction portion 12 and a part of the actuation portion 13. As illustrated in FIG. 2E, the side wall of the cylindrical hollow pipe 60 made of a resin material or a metal material is cut out to form the fixed portion 109, the sliding portion 110, the first suspension portion 111a, and the second suspension portion 111b as the expansion/contraction portion 12, as well as the first wire piece 111c and the second wire piece 111d as the actuation portion 13. The first wire piece 111c is substantially parallel to the closed first suspension portion 111a, and deviated toward the second inner shaft 103 from the first suspension portion 111a in the circumferential direction of the sliding portion 110 (see FIG. 2A). Similarly, the second wire piece 111d is substantially parallel to the closed second suspension portion 111b, and deviated toward the second inner shaft 103 from the second suspension portion 111b in the circumferential direction of the sliding portion 110.

In this case, as described above, the first wire 112a and the first wire piece 111c can be joined to each other such that they overlap with each other in the longitudinal direction of the first inner shaft 102. Similarly, the second wire 112b and the second wire piece 111d can be joined to each other such that they overlap with each other in the longitudinal direction of the first inner shaft 102 (see FIG. 3). Note that the configuration illustrated in FIG. 2E is described in the catheter 100 in FIG. 1 to FIG. 2C, FIG. 3, and FIG. 5A to FIG. 5D.

Figure 2F:
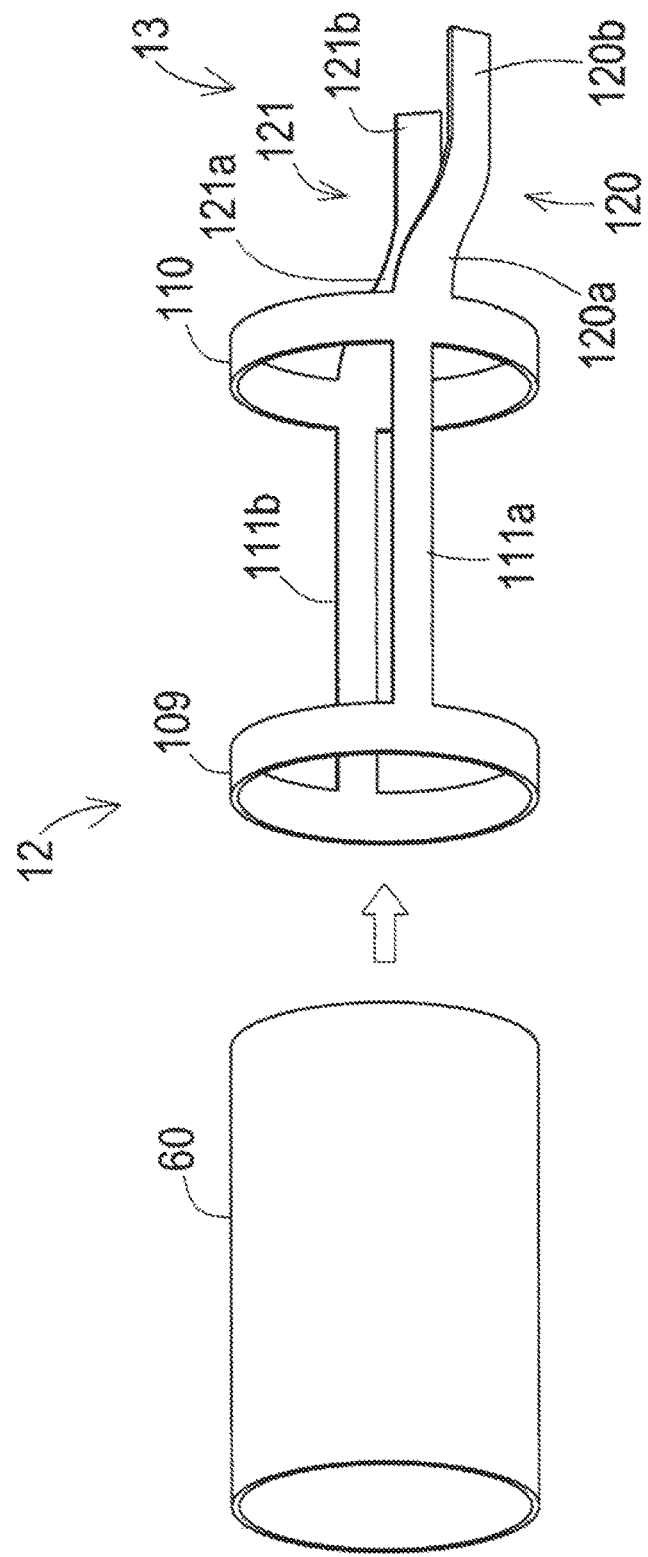
FIG. 2F is a diagram for illustrating another method for integrally forming the expansion/contraction portion and a part of the actuation portion.

FIG. 2F is a diagram for illustrating another method for integrally forming the expansion/contraction portion 12 and a part of the actuation portion 13. As illustrated in FIG. 2F, the side wall of the cylindrical hollow pipe 60 made of a resin material or a metal material is cut out to form the fixed portion 109, the sliding portion 110, the first suspension portion 111a, and the second suspension portion 111b as the expansion/contraction portion 12, as well as a first wire piece 120 and a second wire piece 121 as the actuation portion 13. The first wire piece 120 is composed of a first curved portion 120a, and a first straight portion 120b continuous with the first curved portion 120a. The first curved portion 120a is curved toward the second inner shaft 103 (see FIG. 2A), and the first straight portion 120b extends substantially parallel to the closed first suspension portion 111a. The second wire piece 121 is composed of a second curved portion 121a, and a second straight portion 121b continuous with the second curved portion 121a. The second curved portion 121a is curved toward the second inner shaft 103 (see FIG. 2A), and the second straight portion 121b extends substantially parallel to the closed second suspension portion 111b. Incidentally, the first curved portion 120a and the second curved portion 121a may be formed in a straight shape.

In this case, the first wire 112a and the first straight portion 120b of the first wire piece 120 are joined to each other such that they overlap with each other in the longitudinal direction of the first inner shaft 102. Similarly, the second wire 112b and the second straight portion 121b of the second wire piece 121 are joined to each other such that they overlap with each other in the longitudinal direction of the first inner shaft 102. Joining between the first wire 112a and the first straight portion 120b of the first wire piece 111c or the first wire piece 120 can be achieved by any method. When the first wire 112a, the first wire piece 111c, and the first wire piece 120 are made of a resin, or when the first wire 112a is made of a metal material and the first wire piece 111c and the first wire piece 120 are made of a resin material, or when the first wire 112a is made of a resin material and the first wire piece 111c and the first wire piece 120 are made of a metal material, joining e.g. with an adhesive such as an epoxy adhesive can be adopted. When the first wire 112a, the first wire piece 111c, and the first wire piece 120 are made of a metal material, joining by laser welding, or brazing using a metal solder such as silver solder, gold solder, zinc, Sn—Ag alloy, and Au—Sn alloy can be adopted. The same applies to joining between the second wire 112b and the second straight portion 121b of the second wire piece 111d or the second wire piece 121.

As illustrated in FIG. 3, the first wire 112a joined to the first wire piece 111c (see FIG. 2E) formed by cutting out the side wall of the hollow pipe 60 is inserted into the first wire lumen 118a. The second wire 112b joined to the second wire piece 111d (see FIG. 2E) formed by cutting out the side wall of the hollow pipe 60 is inserted into the second wire lumen 118b. When forming the expansion/contraction portion 12 and a part of the actuation portion 13 by the method illustrated in FIG. 2F, the first wire piece 111c is replaced by the first straight portion 120b of the first wire piece 120, and the second wire piece 111d is replaced by the second straight portion 121b of the second wire piece 121, in the sectional view in FIG. 3. Although FIG. 1, FIG. 2A, FIG. 2B, and FIG. 2C illustrate the configuration that the suspension portion 111 is expanded by pushing the proximal end of the suspension portion 111 toward the distal end while fixing the distal end of the suspension portion 111, it is allowed to take a configuration that the suspension portion 111 is expanded by pulling the distal end of the suspension portion 111 toward the proximal end while fixing the proximal end of the suspension portion 111.

FIG. 4 is a schematic diagram illustrating the imaging sensor 200. The imaging sensor 200 is a long medical device, and is composed of the transducer 201 that transmits and receives ultrasonic waves, the hollow driving cable 202, and a connector 203. An electric wire (not illustrated) is connected to the transducer 201, and the electric wire is connected to a cable 50 through a lumen inside the hollow driving cable 202 and a lumen inside the connector 203 (see FIG. 1). The cable 50 is connected to the imaging console 300.

By operation of the imaging console 300, the transducer 201 disposed on the distal end transmits ultrasonic waves in the radial direction while rotating around the longitudinal axis of the transducer in a body cavity, and receives ultrasonic waves reflected from a living tissue. The transducer 201 transmits the received ultrasonic waves to the imaging console 300 through the aforementioned electric wire and the cable 50. In the recanalization catheter system 1, the imaging sensor 200 is used while inserted into the first lumen 115 of the first inner shaft 102. The imaging sensor 200 is connected to the second dial 105b of the regulator 105 between the distal end and the proximal end of the imaging sensor 200. By operation of the second dial 105b, the transducer 201 arranged on the distal end of the imaging sensor 200 can be moved forward and backward along the longitudinal direction of the first inner shaft 102. The imaging console 300 illustrated in FIG. 1 controls rotation of the transducer 201, and transmission and reception of the ultrasonic waves by the transducer 201, and also converts ultrasonic signals received from the transducer 201 into image signals to display an image on a display 302.

The penetration guide wire 400 (see FIG. 1, and FIG. 2A to FIG. 2C) is a long medical device having a pointed portion on the distal end. The pointed portion has an arrowhead shape or a wedge shape that are tapered from the proximal end side toward the distal end side. The penetration guide wire 400 can penetrate a living tissue by the pointed portion formed on the distal end.

Figure 5B:
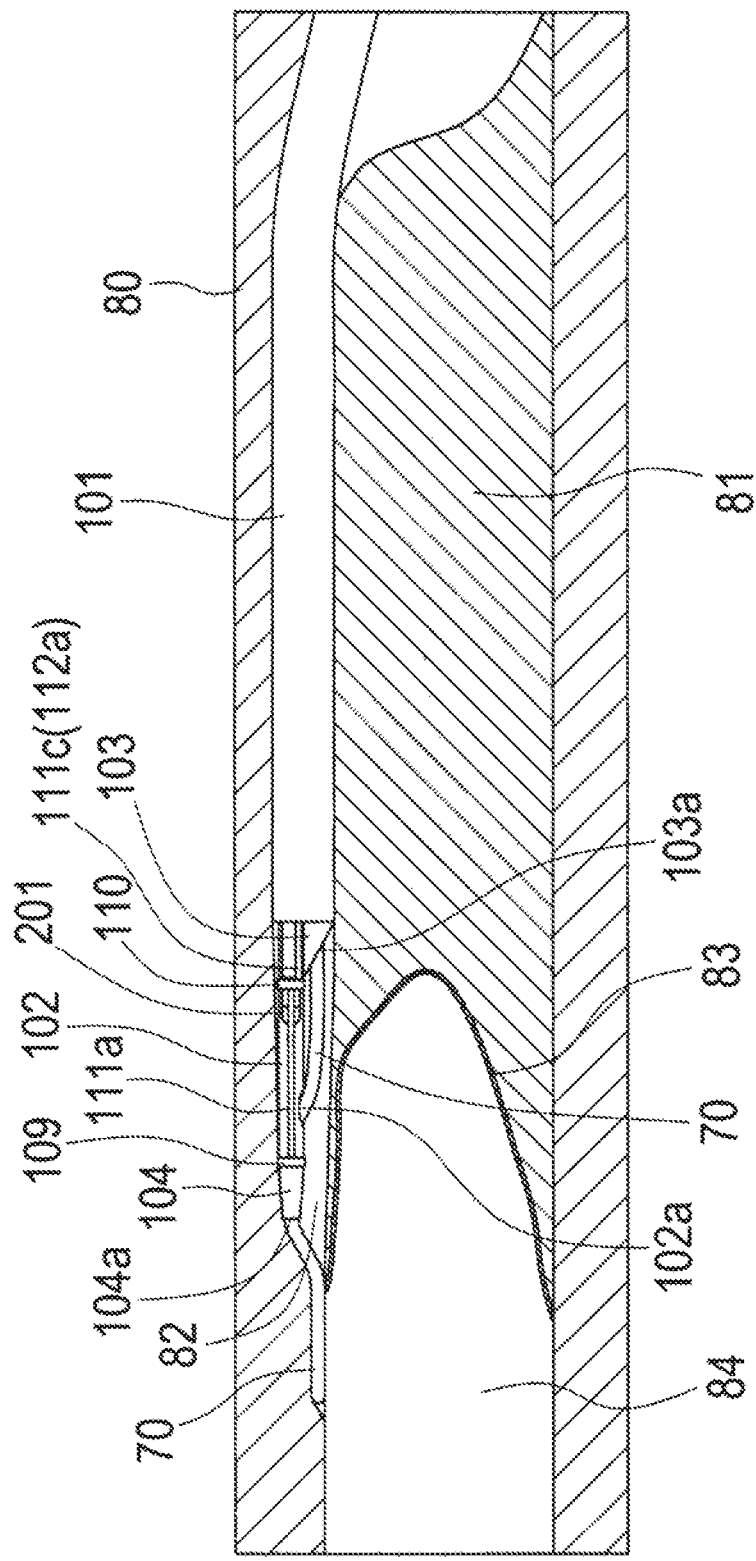
FIG. 5B is a diagram illustrating a state in which the catheter is inserted into the coronary artery along the delivery guide wire.
Figure 5C:
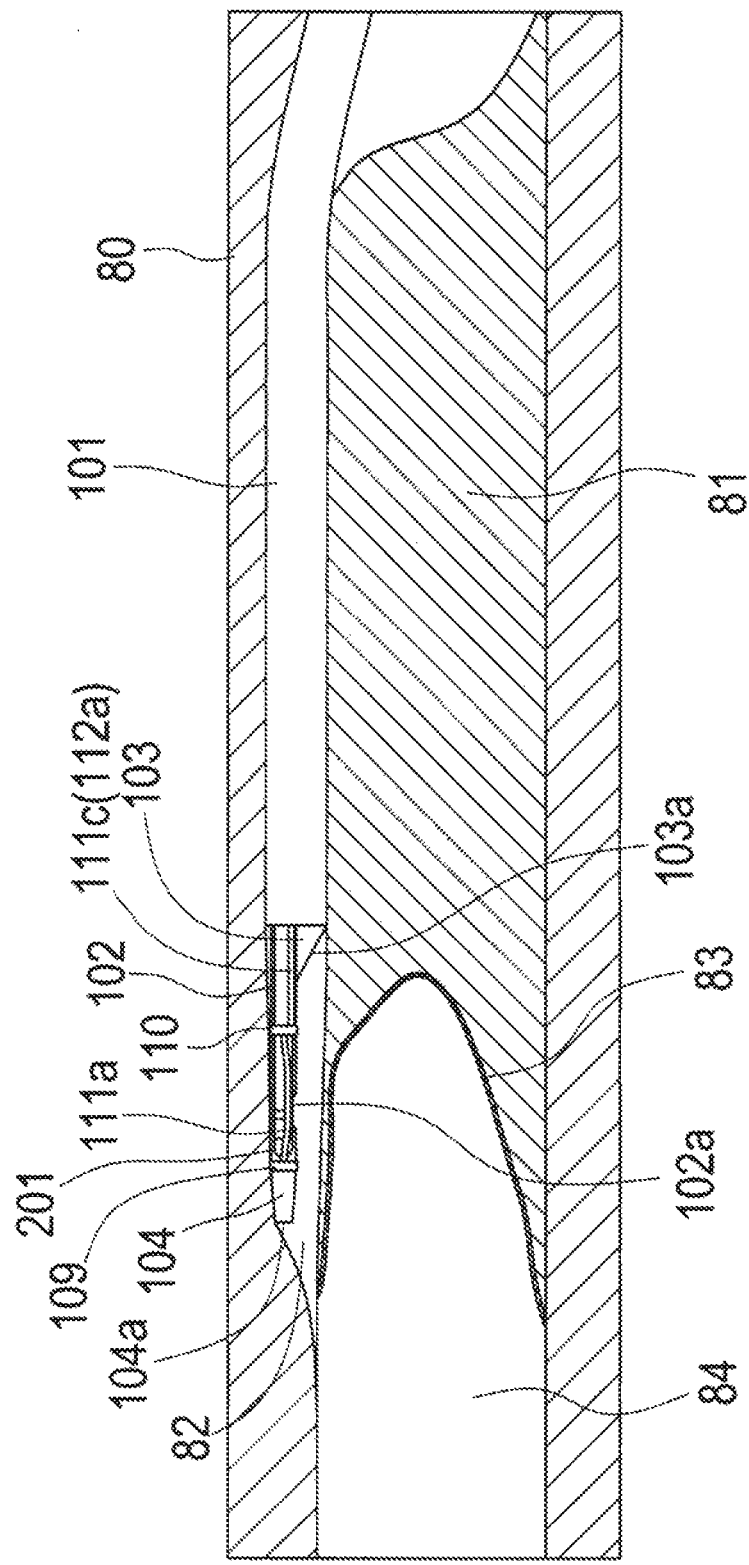
FIG. 5C is a diagram illustrating a state in which a suspension portion of the expansion/contraction portion is expanded.
Figure 5D:
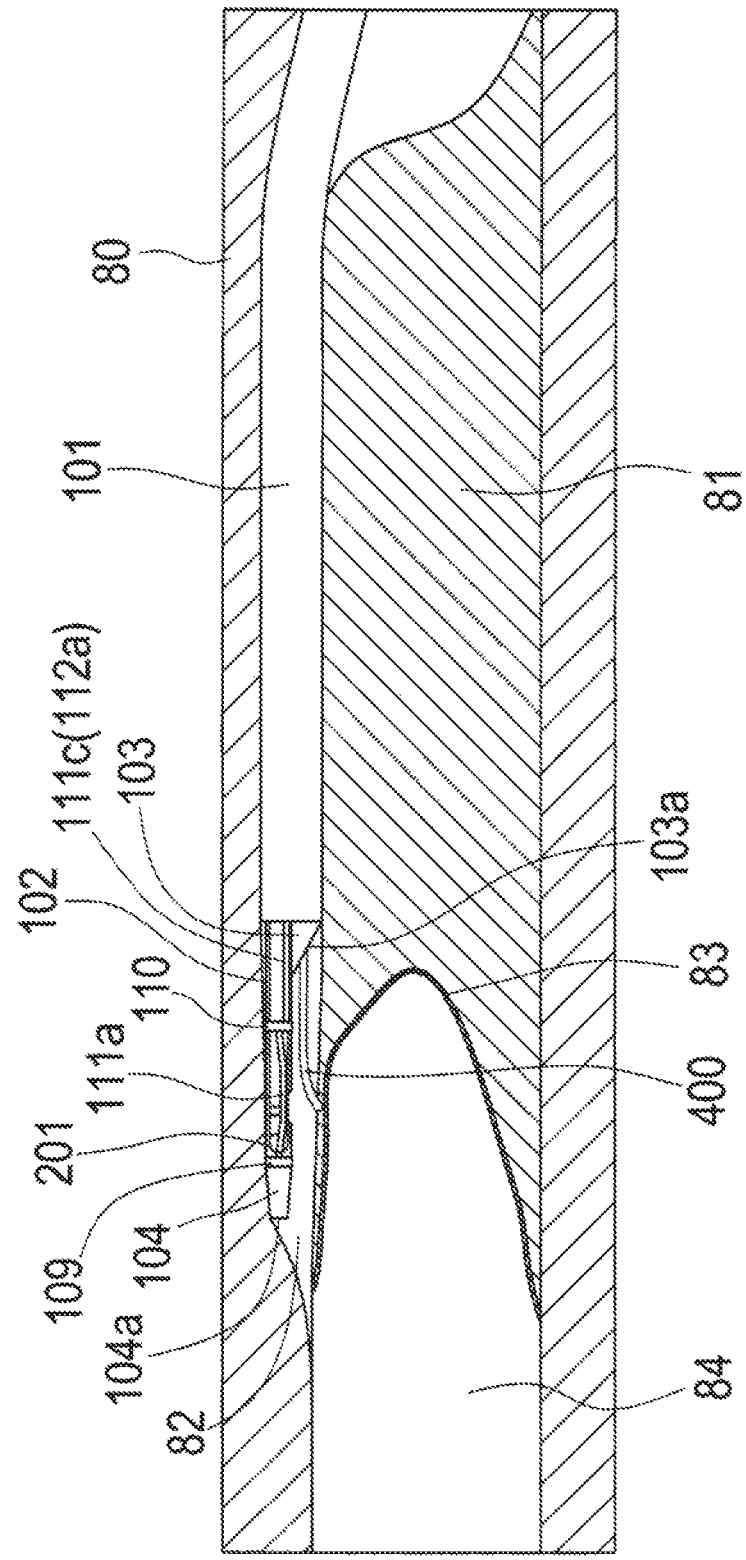
FIG. 5D is a diagram illustrating a state in which a penetration guide wire penetrates a living tissue.

FIGS. 5A-5D are diagrams illustrating examples of using the recanalization catheter system 1. FIG. 5A illustrates a state in which the delivery guide wire 70 is inserted into a coronary artery 80. FIG. 5B illustrates a state in which the delivery guide wire 70 is inserted into the catheter 100, and the catheter 100 is inserted into the coronary artery 80 along the delivery guide wire 70. FIG. 5C illustrates a state in which the suspension portion 111 of the expansion/contraction portion 12 is expanded. FIG. 5D illustrates a state in which the penetration guide wire 400 penetrates a living tissue. Each of FIGS. 5A to 5D illustrates the coronary artery 80 as an example of a living body lumen, a CTO 81 caused in the coronary artery 80, a false cavity 82 formed in or under an intima of the coronary artery 80 (all dissected cavities other than true cavities formed by the delivery guide wire 70), a true cavity 84, and a fibrous cap or plaque 83 (hereinafter simply referred to as "fibrous cap 83") present between the false cavity 82 and the true cavity 84. Incidentally, the fibrous cap 83 is formed in a fiber form on a surface of the CTO lesion in some cases.

FIG. 5A illustrates a state in which the delivery guide wire 70 operated by an operator deviates into the intima of the coronary artery 80 or forms the false cavity 82 under the intima.

As illustrated in FIG. 5B, the operator inserts the proximal end of the delivery guide wire 70 into the second lumen 116 of the second inner shaft 103 from the opening 104a of the distal tip 104 of the catheter 100, through the lumen inside the distal tip 104 and the first lumen 115 of the first inner shaft 102 (see FIG. 3), and through the opening 102a of the first inner shaft 102. Then, the catheter 100 is transported to the false cavity 82 along the delivery guide wire 70, and insides of the CTO lesion and the false cavity 82 are observed with the imaging sensor 200. At this time, the operator transports the catheter 100 in a state in which the transducer 201 of the imaging sensor 200 is positioned immediately near the proximal end of the opening 102a in the first lumen 115 of the first inner shaft 102. This is because the observation site of the imaging sensor 200 is moved by moving the catheter 100. While transporting the catheter 100, the operator confirms an image of the coronary artery 80 from the transducer 201 on the display 302, so that the catheter 100 is disposed at an optimum position for penetration into the true cavity with the penetration guide wire 400.

The operator disposes the catheter 100 at an optimum position, then confirms a position of the delivery guide wire 70 on the image acquired by the imaging sensor 200, and turns the catheter 100 such that the target true cavity confronts the delivery guide wire 70 centering on the catheter 100, the opening 103a as an exit of the penetration guide wire 400 is on the true cavity side and confronts the true cavity. That means, the delivery guide wire 70 functionally acts as a landmark for the exit of the penetration guide wire 400.

The operator operates the first dial 105a of the regulator 105, so that the sliding portion 110 is moved toward the distal end through the first wire 112a and the second wire 112b to extend the suspension portion 111 (the expanded suspension portion 111 is not illustrated in FIG. 5B). Expansion of the suspension portion 111 pushes the living tissue in the false cavity 82, and thereby the catheter 100 is fixed. The operator expands the suspension portion 111 while confirming an expanded position and an expansion degree of the suspension portion 111 by the imaging sensor 200, so that the catheter 100 is fixed at an optimum position for fixing the catheter 100 without excessive expansion of the false cavity.

As illustrated in FIG. 5C, fixation of the catheter 100 is confirmed with the imaging sensor 200, and the delivery guide wire 70 is removed. After removing the delivery guide wire 70, the second dial 105b of the regulator 105 is operated, an optimum site for penetration into the true cavity is observed and determined by advancing and retracting the imaging sensor 200 along the longitudinal direction of the first inner shaft 102.

As illustrated in FIG. 5D, after fixing the catheter 100 by expanding the suspension portion 111, the operator inserts the penetration guide wire 400 into the second lumen 116 of the second inner shaft 103 while confirming the image of the coronary artery 80 from the transducer 201 with the display 302, so that the penetration guide wire 400 protrudes from the opening 103a on the distal end. Subsequently, while confirming the image of the penetration guide wire 400 from the transducer 201 by the display 302, the pointed portion of the penetration guide wire 400 is introduced to the aforementioned optimum site for penetration. Subsequently, the living tissue is penetrated using the pointed portion of the penetration guide wire 400, and the distal end of the penetration guide wire 400 is made to reach the true cavity 84.

The method illustrated in FIG. 5A to FIG. 5D makes it possible to canalize the CTO 81 with the recanalization catheter system 1. Incidentally, in the method illustrated in FIG. 5A to FIG. 5D, e.g. the process of observing the living body lumen and the guide wires 70 and 400 with the imaging sensor 200, and the process of turning the catheter 100 may be omitted. Also, the recanalization catheter system 1 may be used for not only the approach from the false cavity 82 to the true cavity 84 explained in FIG. 5A to FIG. 5D but also the approach of penetrating the CTO from the true cavity 84 on the proximal side to the true cavity 84 on the distal side.

Incidentally, in the first aspect of the disclosed embodiments, the outer shaft 101, the first inner shaft 102, the second inner shaft 103, the first and second wire shafts 117a and 117b, and the sealing member 114 correspond to the "shaft". The distal end face of the second inner shaft 103 exposed from the distal end of the outer shaft 101 (see FIG. 2B) corresponds to the "end face" having the second opening (opening 103a). The imaging sensor 200 corresponds to the "sensor" that acquires information on the living tissue, and the penetration guide wire 400 corresponds to the "guide wire that penetrates the living tissue".

EXAMPLE OF EFFECT

As described above, according to the recanalization catheter system 1 of the first aspect of the disclosed embodiments, in the catheter 100, when the sliding portion 110 is slid toward the fixed portion 109 by the first wire 112a and the second wire 112b (actuation portion 13), the suspension portion 111 expands in the radial direction of the first inner shaft 102 (shaft), so that the catheter 100 can be fixed inside the false cavity 82 (under intima) (see FIG. 5C). In addition, the suspension portion 111 connects the fixed portion 109 fixed to the first inner shaft 102 with the sliding portion 110 slidable on the outer peripheral face of the first inner shaft 102 and has a shape extending in the longitudinal direction of the first inner shaft 102, and therefore the suspension portion 111 has a different configuration from the conventional configuration (expandable and contractible tubular balloon). As a result, the recanalization catheter system 1 according to the first aspect of the disclosed embodiments makes it possible to provide the catheter 100 that can be fixed inside the false cavity by a method different from the conventional method.

Furthermore, since the suspension portion 111 includes the two suspension portions 111 (first suspension portion 111a and second suspension portion 111b), a resistance force against the operation of moving the catheter 100 in the longitudinal direction and the operation of turning the catheter 100 in the circumferential direction can be further enhanced, and the fixation force for the catheter 100 in the false cavity can be further enhanced. In addition, the first suspension portion 111a and the second suspension portion 111b are arranged so as to be opposite to each other as illustrated in FIG. 2B, and individually expand in the radial direction of the shaft as illustrated in FIG. 2C. Thereby, the shape of the expanded suspension portion 111 (expansion/contraction portion 12) can be made to fit the shape of the false cavity 82 having a flat cross-sectional shape. As a result, when the expansion/contraction portion 12 is expanded, unnecessary expansion of the false cavity 82 can be reduced compared to the expansion of the conventional expandable and contractible tubular balloon.

Also, in the catheter 100 according to the first aspect of the disclosed embodiments, the second inner shaft 103 as the shaft further has the second lumen 116 juxtaposed with the first lumen 115 (see FIG. 3). As explained in FIG. 5A to FIG. 5D, a plurality of medical devices can be simultaneously held in one catheter 100, e.g. in such a way that the imaging sensor 200 for acquiring information on the living tissue is inserted into the first lumen 115 and the penetration guide wire 400 for penetrating the living tissue is inserted into the second lumen 116.

Furthermore, among the first lumen 115 and the second lumen 116 extending from the proximal end to the distal end in the first inner shaft 102 and the second inner shaft 103 as the shafts, the second lumen 116 is shorter than the first lumen 115 (see FIG. 1). Thus, the imaging sensor 200 is inserted into the longer first lumen 115, and the transducer 201 of the imaging sensor 200 (site that transmits and receives ultrasonic waves to/from the living tissue) is disposed on the distal end portion of the first lumen 115, so that the distal end portion of the medical device (e.g. delivery guide wire 70, penetration guide wire 400, or the like) inserted into the shorter second lumen 116 can be observed with the imaging sensor 200. Thereby, the operator can recognize a condition inside the living body lumen (e.g. CTO 81) and a position of the distal end portion of the medical device (e.g. delivery guide wire 70, penetration guide wire 400, or the like) in real time only by a two-dimensional image from the imaging sensor 200. That means, the catheter 100 according to the first aspect of the disclosed embodiments makes it possible to achieve a procedure for the imaging sensor 200 under a guide without requiring a skill for separately manipulating a plurality of devices in a blood vessel, and a skill for three-dimensionally reconstructing the imaging sensor 200 image and X-ray images, that have been conventionally required for the procedures of the imaging sensor 200 under the guide (e.g. IVUS Guide). Furthermore, since the catheter 100 according to the first aspect of the disclosed embodiments makes it possible to achieve the procedure only by confirming the image of the imaging sensor 200, a number of acquirements of the X-ray images can also be decreased, and it can be expected that an exposure dose to an operator and a patient associated with X-ray photography is decreased, and an amount of a contrast medium used for the X-ray photography is decreased.

Also, in the catheter 100 according to the first aspect of the disclosed embodiments, the second inner shaft 103 as a shaft has an end face where the opening 103a (second opening) communicating between the distal end portion of the second lumen 116 and the outside (see FIG. 2B). Thereby, as illustrated in FIG. 5B, the proximal end portion of the delivery guide wire 70 is taken out from the opening 102a (first opening), and then the proximal end portion of the delivery guide wire 70 is inserted into the second lumen 116 from the opening 103a, so that the delivery guide wire 70 can be fixed to the distal end portion of the first inner shaft 102 as the shaft. Thus, by fixation of the delivery guide wire 70, the delivery guide wire 70 can be oriented constantly in a certain direction relative to the catheter 100 on the image acquired by the imaging sensor 200. As a result, the operator can control the catheter 100 such that the position of the target site relative to the catheter 100, where the penetration guide wire 400 penetrates the living tissue, is optimized (optimum angle), by advancing/retracting and turning the catheter 100 relative to the delivery guide wire 70 while confirming the image from the imaging sensor 200.

Furthermore, for the purpose of fixing the delivery guide wire 70, the distal end portion of the first lumen 115 for the imaging sensor 200 is used. In other words, the first lumen 115 is shared by the delivery guide wire 70 and imaging sensor 200. Thus, the catheter 100 can be reduced in diameter, and can be easily inserted into the living body lumen (e.g. into the coronary artery 80, the CTO 81, or the like), compared to a case of disposing a separate lumen for fixing the delivery guide wire 70. Furthermore, as illustrated in FIG. 5D, when the penetration guide wire 400 penetrates the living tissue, the distal end portion of the penetration guide wire 400 is protruded outward from the opening 103a (second opening) while the penetration guide wire 400 is inserted into the second lumen 116, so that the distal end portion of the penetration guide wire 400 can confront the target site while obtaining a backup force from the first inner shaft 102.

Additionally, in the catheter 100 according to the first aspect of the disclosed embodiments, the expansion/contraction portion 12 (fixed portion 109, sliding portion 110, suspension portion 111) is disposed in the first inner shaft 102 forming the first lumen 115. Thus, when the suspension portion 111 of the expansion/contraction portion 12 is made of a material having a difference in an acoustic impedance from the living tissue, a state of the expanded suspension portion 111 can be observed by the imaging sensor 200 inserted into the first lumen 115, and therefore the suspension portion 111 can be safely expanded while suppressing injury in the living body lumen associated with overexpansion of the suspension portion 111. In addition, since the expansion/contraction portion 12 is made of a radiopaque material, the expansion/contraction portion 12 can be made to functionally act as an orientation marker for x-ray-fluoroscopically confirming a posture and an orientation of the catheter 100 by imaging the expansion/contraction portion 12 on an X-ray image obtained by X-ray photography.

Furthermore, even after fixing the catheter 100, an image acquisition site can be moved by moving the imaging sensor 200 in the first lumen 115. Thus, a positional relationship between the distal end portion of the penetration guide wire 400 and the target site for penetration can be observed by conforming the image acquisition site to the distal end portion of the penetration guide wire 400. As a result, when penetrating the target site, a number of acquisitions of X-ray images can be minimized.

In general, the imaging sensor 200 that is inserted into the first lumen 115 is larger in diameter than the medical device (e.g. delivery guide wire 70, penetration guide wire 400, or the like) that is inserted into the second lumen 116. In the catheter 100 according to the first aspect of the disclosed embodiments, the diameter of the first lumen 115 is larger than the diameter of the second lumen 116 (see FIG. 3). Thus, each diameter of the first and second lumens can be conformed to a thickness of each device inserted into each lumen, and furthermore errors during insertion of the device can be suppressed and the catheter 100 can be reduced in diameter compared to a case in which the diameters of the first and second lumens are the same. Since the catheter 100 includes the braid 108 disposed inside the outer shaft 101 (in the wall portion of the shaft), a torque transmission performance of the catheter 100 can be improved. In addition, since the braid 108 is made of a radiopaque material, a reinforcing member can be imaged on an X-ray image obtained by X-ray photography.

B. Second Aspect

Figure 6A:
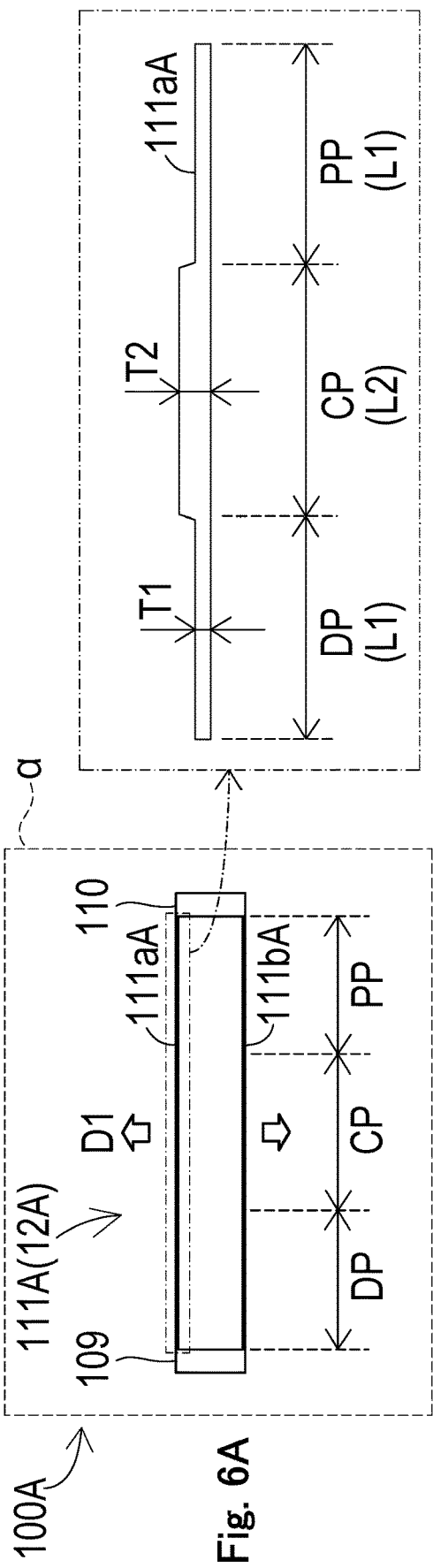
FIGS. 6A and 6B are explanatory diagrams illustrating configurations of an expansion/contraction portion according to a second aspect of the disclosed embodiments.
Figure 6B:
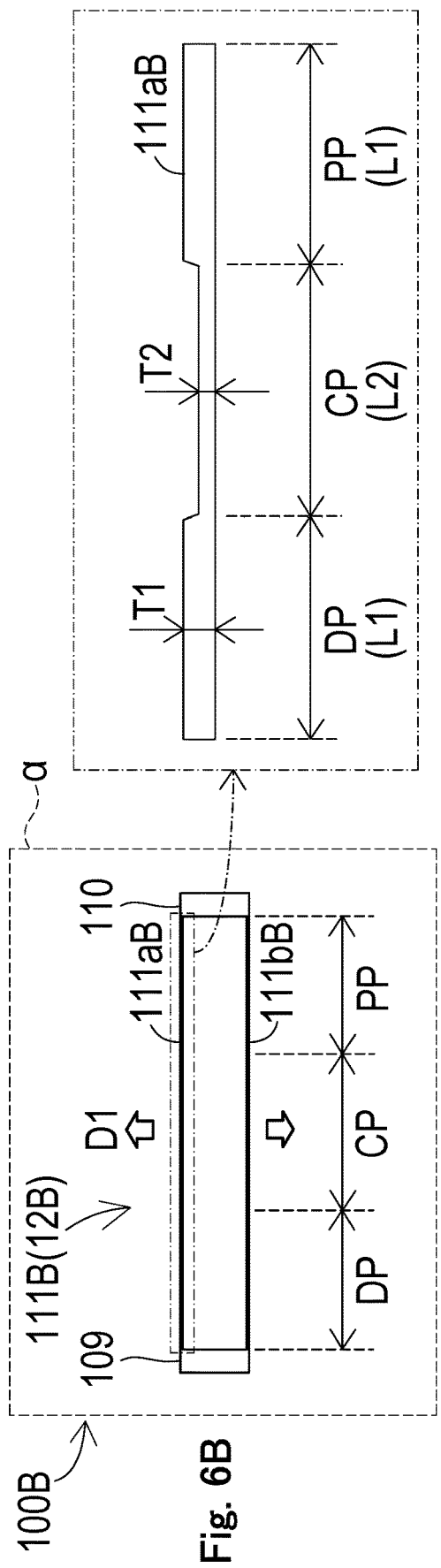

FIGS. 6A and 6B are explanatory diagrams illustrating configurations of expansion/contraction portions 12A and B according to as second aspect of the disclosed embodiments. FIG. 6A illustrates an example of a configuration of the expansion/contraction portion 12A, and FIG. 6B illustrates an example of a configuration of the expansion/contraction portion 12B. In each figure, on the left side, the contracted (not expanded) expansion/contraction portions 12A and 12B on the virtual plane α are illustrated, and on the right side, enlarged views of first suspension portions 111aA and 11aB are illustrated. A catheter 100A according to the second aspect of the disclosed embodiments illustrated in FIG. 6A includes the expansion/contraction portion 12A having a configuration different from the first aspect of the disclosed embodiments.

The expansion/contraction portion 12A includes a suspension portion 111A composed of the first suspension portion 111aA and a second suspension portion 111bA. A catheter 100B according to the second aspect of the disclosed embodiments illustrated in FIG. 6B includes the expansion/contraction portion 12B having a configuration different from the first aspect of the disclosed embodiments. The expansion/contraction portion 12B includes a suspension portion 111B composed of the first suspension portion 111aB and a second suspension portion 111bB. Herein, the first suspension portions 111aA and 11aB, and the second suspension portions 111bA and 11bB are constitutively symmetrical with each other relative to an axis line (center) of the catheter 100A. Thus, hereinafter, configurations of the suspension portions 111A and 111B will be explained with reference to the enlarged views of the first suspension portions 111aA and 111aB on the right side.

As illustrated in FIGS. 6A and 6B, each of the suspension portion 111A and the suspension portion 111B includes a distal end portion DP positioned on the distal end side, a central portion CP, and a proximal end portion PP positioned on the proximal end side, in the longitudinal direction of the catheter 100A or 100B respectively. The central portion CP is positioned between the distal end portion DP and the proximal end portion PP. In the suspension portions 111A and 111B according to the second aspect of the disclosed embodiments, a rigidity of the central portion CP is relatively different from rigidities of the distal end portion DP and the proximal end portion PP. Specifically, in the example of FIG. 6A, the suspension portion 111A is configured such that a thickness T2 of the central portion CP in an expanding direction of the suspension portion 111A (white arrows on the left side of FIG. 6A, hereinafter also referred to as "expansion direction D1") is larger than thicknesses T1 of the distal end portion DP and the proximal end portion PP. In such a way, the rigidity of the central portion CP can be made higher than the rigidities of the distal end portion DP and the proximal end portion PP. In addition, in the example of FIG. 6B, the suspension portion 111B is configured such that the thickness T2 of the central portion CP in the expansion direction D1 is smaller than the thicknesses T1 of the distal end portion DP and the proximal end portion PP. In such a way, the rigidity of the central portion CP can be made lower than the rigidities of the distal end portion DP and the proximal end portion PP. Incidentally, the thicknesses T1 and T2 can be arbitrarily determined as long as they are different.

In addition, as illustrated in FIG. 6A and FIG. 6B, the suspension portions 111A and 111B are configured such that a length L1 of the distal end portion DP and a length L1 of the proximal end portion PP are substantially the same in the longitudinal direction of the catheters 100A and 100B, and a length L2 of the central portion CP is longer than the length L1 of the distal end portion DP. Incidentally, the lengths L1 and L2 can be arbitrarily determined.

Figure 7:
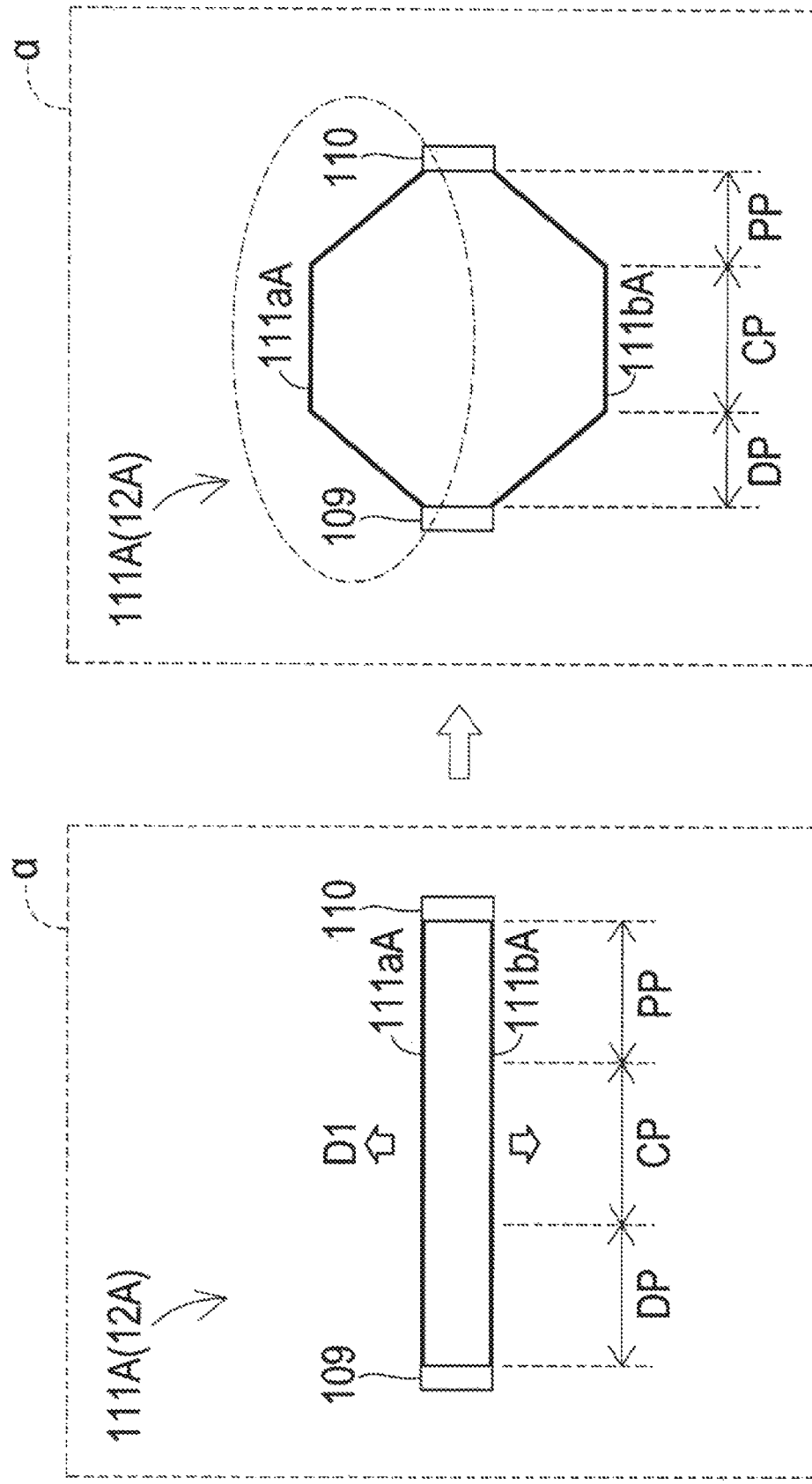
FIG. 7 is an explanatory diagram illustrating a state in which the expansion/contraction portion according to the second aspect of the disclosed embodiments.

FIG. 7 is an explanatory diagram illustrating a state that the expansion/contraction portion 12A according to the second aspect of the disclosed embodiments expands. In the suspension portion 111A according to the second aspect of the disclosed embodiments explained in FIG. 6A, the rigidity of the central portion CP is relatively different from the rigidities of the distal end portion DP and the proximal end portion PP, as described above. Thus, a shape of the suspension portion 111A expanding in the expansion direction D1 (opened shape viewed from the bottom side) can be a substantially trapezoidally expanding shape when each of a boundary between the central portion CP and the distal end portion DP and a boundary between the central portion CP and the proximal end portion PP is bent, and the central portion CP is away from the outer peripheral face of the first inner shaft 102 substantially parallel to the longitudinal direction (the right side of FIG. 7, circle with dot and dash line). Incidentally, similarly, the suspension portion 111B according to the second aspect of the disclosed embodiments explained in FIG. 6B can also have substantially trapezoidally expanding shape because the rigidity of the central portion CP is relatively different from the rigidity of the distal end portion DP and the proximal end portion PP.

FIGS. 8A and 8B are explanatory diagrams illustrating a state of the expansion/contraction portion 12A in the false cavity 82. FIG. 8A illustrates a state in which the expansion/contraction portion 12A according to the second aspect of the disclosed embodiments explained in FIG. 6A is expanded, and FIG. 8B illustrates a state in which an expansion/contraction portion 12X of a comparative example is expanded. Since FIGS. 8A and 8D illustrate the cross section of the coronary artery 80 explained in FIGS. 5A-5D, an extending direction of a center O of the coronary artery 80 in FIGS. 8A and 8B coincides with the longitudinal direction of the catheter 100A. A catheter 100X of a comparative example includes a tubular balloon 111X that is expandable and contractible as the expansion/contraction portion 12X, instead of the fixed portion 109, the sliding portion 110, and the suspension portion 111A.

As illustrated in FIG. 8A, since the false cavity 82 is a dissociated cavity formed by partial exfoliation of a vascular tissue e.g. a cavity between an intimal tissue layer and an adventitial tissue layer of the coronary artery 80, the false cavity 82 has a flatter cross-sectional shape compared to the true cavity 84. In this regard, as for the catheter 100A according to the second aspect of the disclosed embodiments, the suspension portion 111A (first suspension portion 111aA, second suspension portion 111bA) made of a plate-shaped member extending in the longitudinal direction expands in the expansion direction D1 to push a wall face (living tissue) of the false cavity 82, so that the catheter 100A is fixed. Thus, the catheter 100A can be fixed inside the false cavity 82 without expanding the false cavity 82, by conforming the longitudinal direction of the flat false cavity 82 to the expansion direction D1 of the suspension portion 111A in the cross-section as illustrated in FIG. 8A.

Additionally, in the suspension portion 111A according to the second aspect of the disclosed embodiments, the rigidity of the central portion CP is relatively different from the rigidities of the distal end portion DP and the proximal end portion PP positioned on both ends of the central portion CP, and therefore the shape of the suspension portion 111A expanding in the expansion direction D1 can be a substantially trapezoid (the right side of FIG. 7, circle with dot and dash line). Thus, a contact area where the suspension portion 111A is in contact with the wall face (living tissue) of the false cavity 82 can be increased compared to a case without the difference in rigidity. Thus, a risk of enlarging the false cavity 82 due to expansion of the suspension portion 111A can be reduced, and furthermore injury of the living body due to the suspension portion 111A when operating of turning the catheter 100A in the circumferential direction can be suppressed. Also, since a friction resistance with the living tissue wall face can be enhanced as the contact area increases, a resistance force against the operation of moving the catheter 100A in the longitudinal direction and the operation of turning the catheter 100A in the circumferential direction can be enhanced. In other words, a force to fix the catheter 100A can be enhanced.

Furthermore, in the suspension portion 111A according to the second aspect of the disclosed embodiments, the thickness T2 of the central portion CP is made relatively different from the thicknesses T1 of the distal end portion DP and the proximal end portion PP, so that they can have different rigidities (see FIGS. 6A and 6B). A resistance force against the operation of turning the suspension portion 111A in the circumferential direction can be enhanced by varying the rigidity depending on the thickness (wall thickness) as described above.

Furthermore, in the suspension portion 111A according to the second aspect of the disclosed embodiments, the lengths L1 of the distal end portion DP and the proximal end portion PP in the longitudinal direction are substantially the same, and the length L2 of the central portion CP is larger than the length L1 of the distal end portion DP (see FIGS. 6A and 6B). Thus, the contact area where the suspension portion 111A is in contact with the living tissue can be increased, and a fixation force for the catheter 100A can be further enhanced. As a result, for example, even when not only the imaging sensor 200 for acquiring information on the living tissue but also a medical device requiring a backup force such as the penetration guide wire 400 for penetrating the living tissue are used while inserted into the catheter 100A, the catheter 100A can be fixed in the false cavity 82 (under intima), and deviation of the catheter 100A can be suppressed. Incidentally, also for the suspension portion 111B according to the second aspect of the disclosed embodiments explained in FIG. 6B, the same effects as the aforementioned effects can be exhibited.

On the other hand, as illustrated in FIG. 8B, in the conventional catheter 100X presented as a comparative example, the expansion direction of the balloon 111X is a direction DX radially expanding from the center (FIG. 8B, black arrow). Thus, expansion of the balloon 111X presses the wall face (living tissue) of the flat false cavity 82, and therefore the false cavity 82 may be expanded. In addition, since the balloon 111X easily turns in the circumferential direction in the false cavity 82, the resistance force against the operation of moving the catheter 100X in the longitudinal direction and the operation of turning the catheter 100X in the circumferential direction cannot be sufficiently obtained.

C. Third Aspect

Figure 9A:
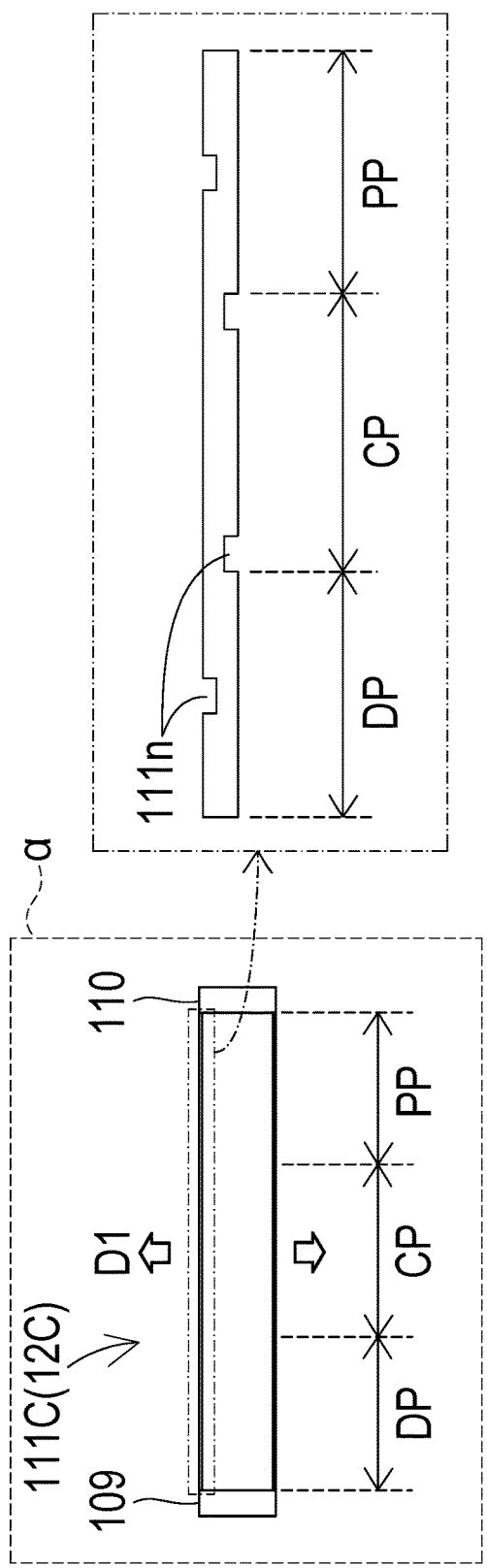
FIGS. 9A and 9B are explanatory diagrams illustrating configurations of an expansion/contraction portion according to a third aspect of the disclosed embodiments.
Figure 9B:
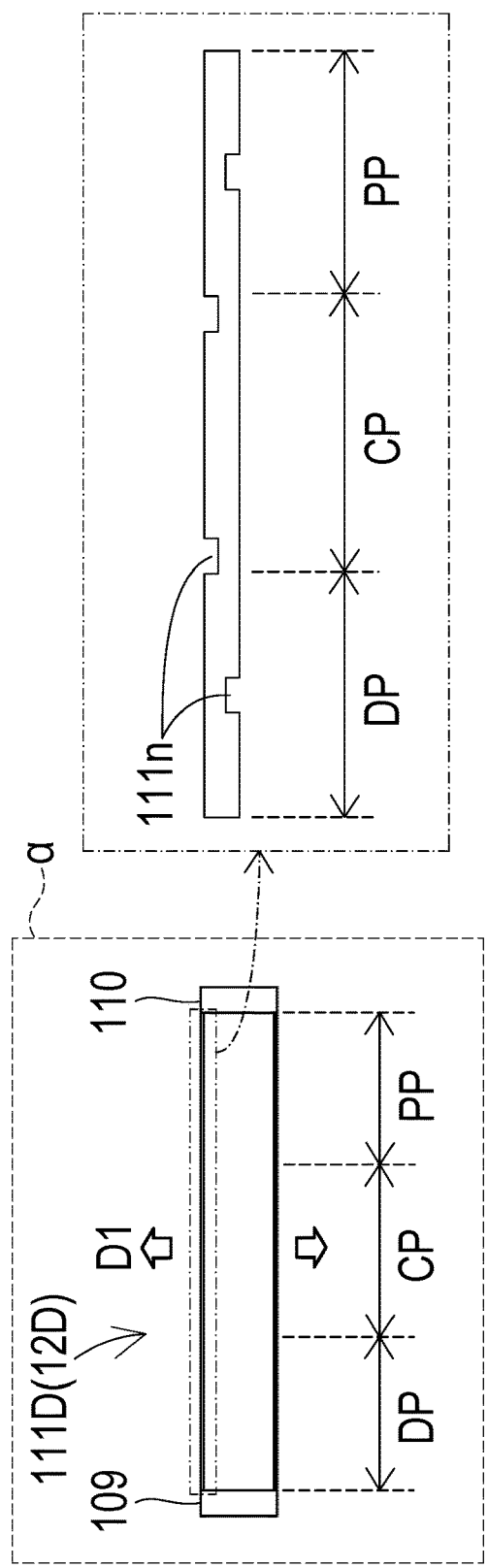

FIGS. 9A and 9B are exemplary diagrams illustrating configurations of expansion/contraction portions 12C and D according to a third aspect of the disclosed embodiments. FIG. 9A illustrates an example of the configuration of the expansion/contraction portion 12C, and FIG. 9B illustrates an example of the configuration of the expansion/contraction portion 12D. Regarding the expansion/contraction portions 12C and 12D according to the third aspect of the disclosed embodiments, in suspension portions 111C and 111D, a rigidity of a central portion CP is made different from rigidities of a distal end portion DP and a proximal end portion PP by a method different from that in the second aspect of the disclosed embodiments.

Specifically, in the example of FIG. 9A, the suspension portion 111C is configured such that one notch 111n is formed on each substantially central portion of outer side faces (outer peripheral faces) of the distal end portion DP and the proximal end portion PP. On the other hand, two notches 111n are formed on both end portions of an inner side face (inner peripheral face) of the central portion CP. In such a way, the rigidity of the central portion CP can be made different from the rigidities of the distal end portion DP and the proximal end portion PP. Additionally, in the example of FIG. 9B, in the suspension portion 111D, one notch 111n is formed on each substantially central portion of inner side faces of the distal end portion DP and the proximal end portion PP, and two notches 111n are formed on both end portions of an outer side face of the central portion CP. Also in such a way, the rigidity of the central portion CP can be made different from the rigidities of the distal end portion DP and the proximal end portion PP.

The rigidity of the central portion CP may be made different from the rigidities of the distal end portion DP and the proximal end portion PP by a means other than the thickness, such as a number and positions of the notches 111n formed in the suspension portions 111C and 111D as in the third aspect of the disclosed embodiments. Also in such a way, the same effect as of the second aspect of the disclosed embodiments can be exhibited. Additionally, in the suspension portions 111C and 111D according to the third aspect of the disclosed embodiments, the suspension portions 111C and 111D can be bent at a position of the notch 111n, which is made more brittle than other areas, and therefore it is easy to control the shapes of the expanded suspension portions 111C and 111D depending on the position having the notch 111n.

D. Fourth Aspect

Figure 10A:
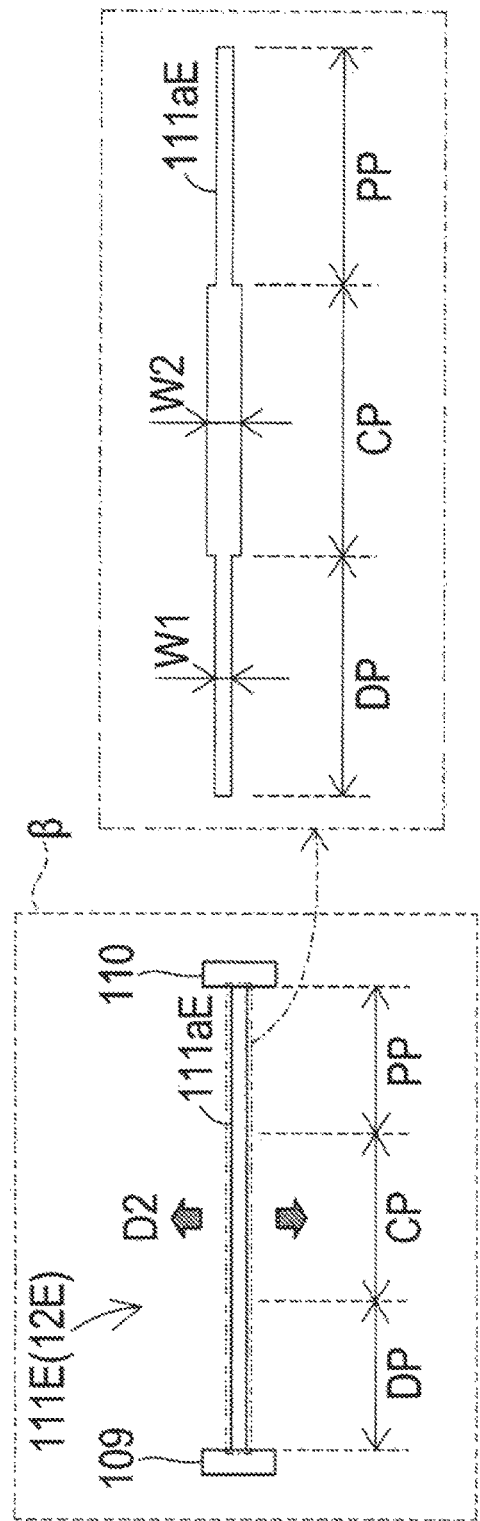
FIGS. 10A and 10B are explanatory diagrams illustrating configurations of an expansion/contraction portion according to a fourth aspect of the disclosed embodiments.
Figure 10B:
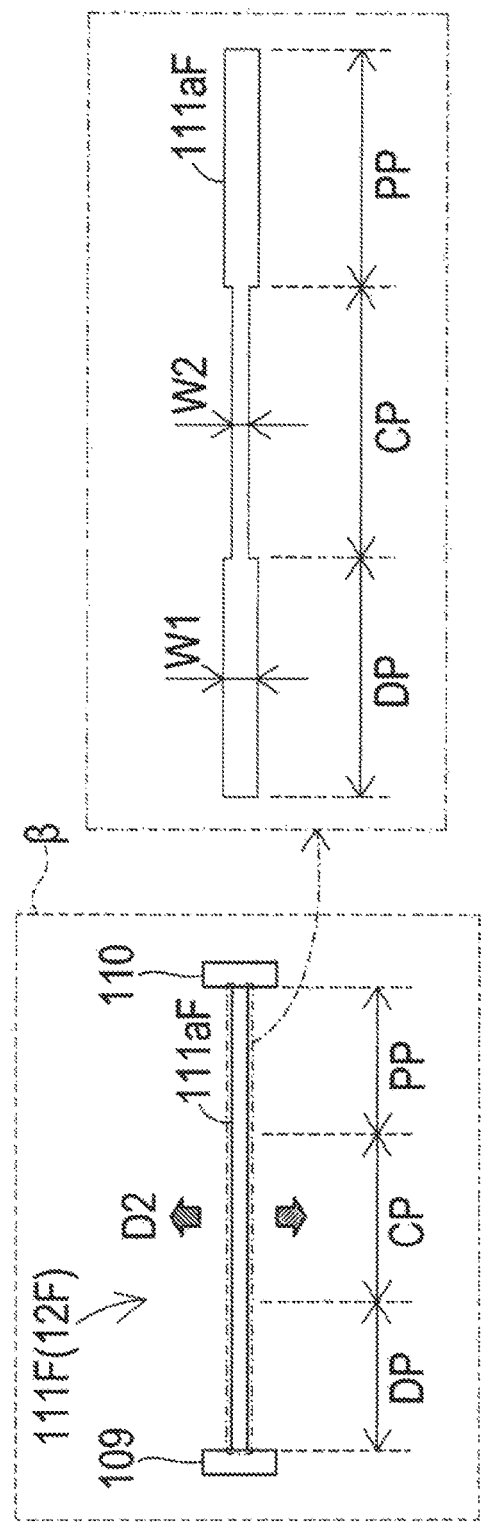

FIGS. 10A and 10B are explanatory diagrams illustrating configurations of the expansion/contraction portions 12E and 12F according to a fourth aspect of the disclosed embodiments. FIG. 10A illustrates an example of the configuration of the expansion/contraction portion 12E, and FIG. 10B illustrates an example of the configuration of the expansion/contraction portion 12F. In each figure, on the left side, the contracted expansion/contraction portions 12E and 12F on the virtual plane β substantially perpendicular to the virtual plane α illustrated in FIGS. 6A and 6B are illustrated, and on the right side, enlarged views of first suspension portions 111aE and 111aF are illustrated. Regarding the expansion/contraction portions 12E and 12F according to the fourth aspect of the disclosed embodiments, in suspension portions 111E and 111F, a rigidity of a central portion CP is made different from rigidities of a distal end portion DP and a proximal end portion PP by a method different from that in the second aspect of the disclosed embodiments.

Specifically, in the example of FIG. 10A, the suspension portion 111E is configured such that a width W2 of the central portion CP in a direction orthogonal to the expansion direction D1 (FIGS. 6A and 6B) of the suspension portion 111E (an arrow diagonally hatched on the left side of FIG. 10A, hereinafter referred to as "orthogonal direction D2") is larger than widths W1 of the distal end portion DP and the proximal end portion PP. In such a way, the rigidity of the central portion CP can be made higher than the rigidities of the distal end portion DP and the proximal end portion PP. In the example of FIG. 10B, the suspension portion 111F is configured such that the width W2 of the central portion CP in the orthogonal direction D2 is smaller than the widths W1 of the distal end portion DP and the proximal end portion PP. In such a way, the rigidity of the central portion CP can be made lower than the rigidities of the distal end portion DP and the proximal end portion PP. Incidentally, the widths W1 and W2 can be arbitrarily determined as long as they are different.

Figure 11A:
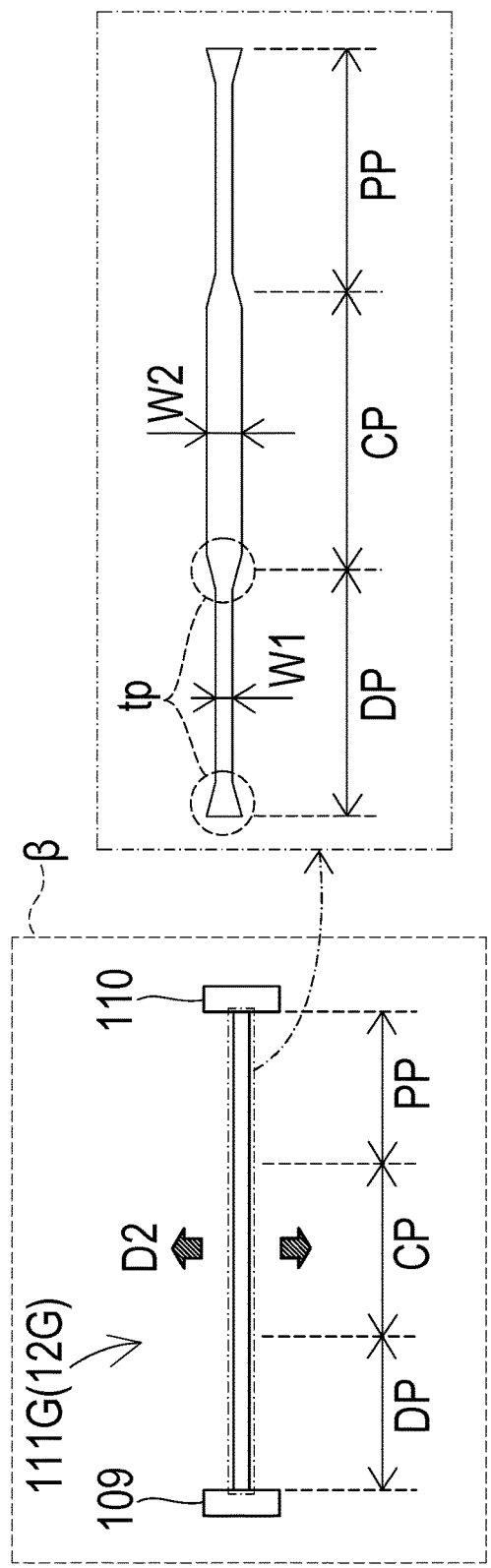
FIGS. 11A and 11B are explanatory diagrams illustrating other configurations of the expansion/contraction portion according to the fourth aspect of the disclosed embodiments.
Figure 11B:
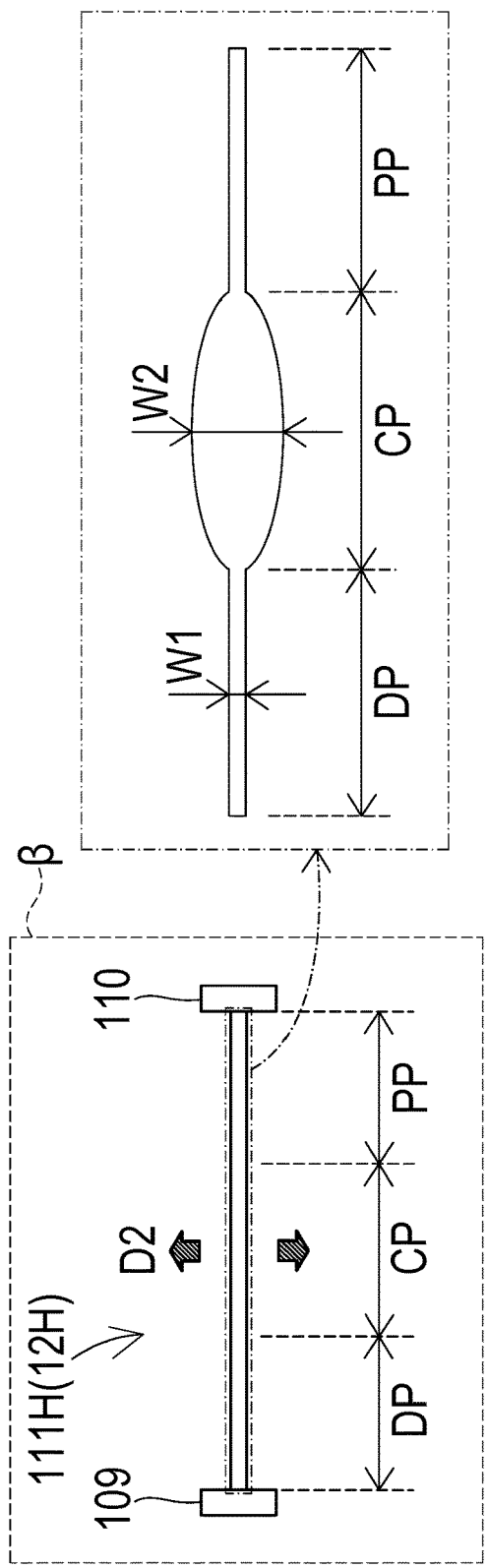

FIGS. 11A and 11B are explanatory diagrams illustrating configurations of expansion/contraction portions 12G and 12H according to a fourth aspect of the disclosed embodiments. FIG. 11A illustrates an example of the configuration of the expansion/contraction portion 12G, and FIG. 11B illustrates an example of the configuration of the expansion/contraction portion 12H. In the example of FIG. 11A, a suspension portion 111G further includes tapered portions tp having a gradually changing width at boundaries between the respective portions, in addition to the difference between the widths W1 and W2 explained in FIGS. 10A and 10B. Specifically, the tapered portions tp are formed on a distal end portion of the distal end portion DP joined to the fixed portion 109, a boundary portion between the distal end portion DP and the central portion CP, a boundary portion between the central portion CP and the proximal end portion PP, and a proximal end portion of the proximal end portion PP joined to the sliding portion 110. In such a way, corners on the boundaries between the respective portions can be eliminated, so that injury of the wall face (living tissue) of the false cavity 82 due to the expanded suspension portion 111G can be suppressed.

In the example of FIG. 11B, a suspension portion 111H further has a substantially elliptical shape such that the width W2 of the central portion CP is gradually broadened from the distal end portion DP and the proximal end portion PP toward the middle portion, in addition to the difference between the widths W1 and W2 explained in FIGS. 10A and 10B. Incidentally, although the distal end portion DP and the proximal end portion PP have a plate shape similar to that shown in FIGS. 10A and 10B, the shapes of the distal end portion DP and the proximal end portion PP can be arbitrarily changed. In such a way, a contact area of the central portion CP with the wall face (living tissue) of the false cavity 82 can be further increased in the expanded suspension portion 111H, so that the fixation force for the catheter can be further enhanced.

The rigidity of the central portion CP may be made different from the rigidities of the distal end portion DP and the proximal end portion PP by a means other than the thickness, such as the widths W1 and W2 of the suspension portions 111E, 111F, 111G, and 111H in the orthogonal direction D2 as in the fourth aspect of the disclosed embodiments. Also in such a way, the same effect as of the second aspect of the disclosed embodiments can be exhibited. In the suspension portions 111E, 111F, 111G, and 111H in the fourth aspect of the disclosed embodiments, a structure of the suspension portions 111E, 111F, 111G, and 111H which is easily laser-processed can be obtained by making the difference in rigidity depending on the widths W1 and W2 in the orthogonal direction D2.

E. Fifth Aspect

FIGS. 12A and 12B are explanatory diagrams illustrating configurations of expansion/contraction portions 12I and 12J according to a fifth aspect of the disclosed embodiments. FIG. 12A illustrates an example of the configuration of the expansion/contraction portion 12I, and FIG. 12B illustrates an example of the configuration of the expansion/contraction portion 12J. Regarding the expansion/contraction portions 12I and 12J according to the fifth aspect of the disclosed embodiments, in suspension portions 111I and 111J, a rigidity of a central portion CP is made different from rigidities of a distal end portion DP and a proximal end portion PP by a method different from that in the second aspect of the disclosed embodiments.

Specifically, in the example of FIG. 12A, the suspension portion 111I has a plurality of circular holes 111h formed on the distal end portion DP and the proximal end portion PP, meanwhile the central portion CP has no holes. In such a way, the rigidity of the central portion CP can be made higher than the rigidities of the distal end portion DP and the proximal end portion PP. In addition, in the example of FIG. 12B, the suspension portion 111J has the plurality of circular holes 111h formed on the central portion CP, meanwhile the distal end portion DP and the proximal end portion PP have no holes. In such a way, the rigidity of the central portion CP can be made lower than the rigidities of the distal end portion DP and the proximal end portion PP. Incidentally, the hole 111h may be a through-hole that penetrates the suspension portions 111I and 111J, or a non-through-hole that does not penetrate, or a tapered hole having different hole diameters of the upper part and the lower part. Additionally, in the example of FIGS. 12A and 12B, on the suspension portions 111I and 111J, there are three rows of the holes 111h arranged in the transverse direction of the suspension portions 111I and 111J. However, one or a plurality of holes 111h may be formed on the suspension portions 111I and 111J. When the plurality of holes 111h are formed, arrangement of each hole 111h may be arbitrarily changed.

FIGS. 13A and 13B are explanatory diagrams illustrating other configurations of expansion/contraction portions 12K and 12L according to a fifth aspect of the disclosed embodiments. FIG. 13A illustrates an example of the configuration of the expansion/contraction portion 12K, and FIG. 13B illustrates an example of the configuration of the expansion/contraction portion 12L. In the example of FIG. 13A, a plurality of substantially elliptical holes 111hK are juxtaposed in a longitudinal direction of a suspension portion 111K. In the example of FIG. 13B, a plurality of straight holes 111hL (slits 111hL) extending in the longitudinal direction are juxtaposed in a transverse direction of a suspension portion 111L. Incidentally, while the holes 111hK are formed on the central portion CP of the suspension portion 111K as in the example of FIG. 12B, the distal end portion DP and the proximal end portion PP may have no holes. Similarly, although the holes 111hL are formed on the central portion CP of the suspension portion 111L, the distal end portion DP and the proximal end portion PP may have no holes. In addition, the arrangement of each hole 111hK and each hole 111hL may be arbitrarily changed.

The rigidity of the central portion CP may be made different from the rigidities of the distal end portion DP and the proximal end portion PP by a means other than the thickness, such as the holes 111h, 111hK, 111hL formed on either the central portion CP, or the distal end portion DP and the proximal end portion PP of the suspension portions 111I, 111J, 111K, and 111L as in the fifth aspect of the disclosed embodiments. Also in such a way, the same effect as in the second aspect of the disclosed embodiments can be exhibited. Additionally, in the suspension portions 111I, 111J, 111K, and 111L according to the fifth aspect of the disclosed embodiments, a resistance force against the operation of turning the suspension portions 111I, 111J, 111K, and 111L in the circumferential direction can be enhanced by making a difference in rigidity depending on the presence or absence of the holes 111h, 111hK, and 111hL.

F. Sixth Aspect

Figure 14A:
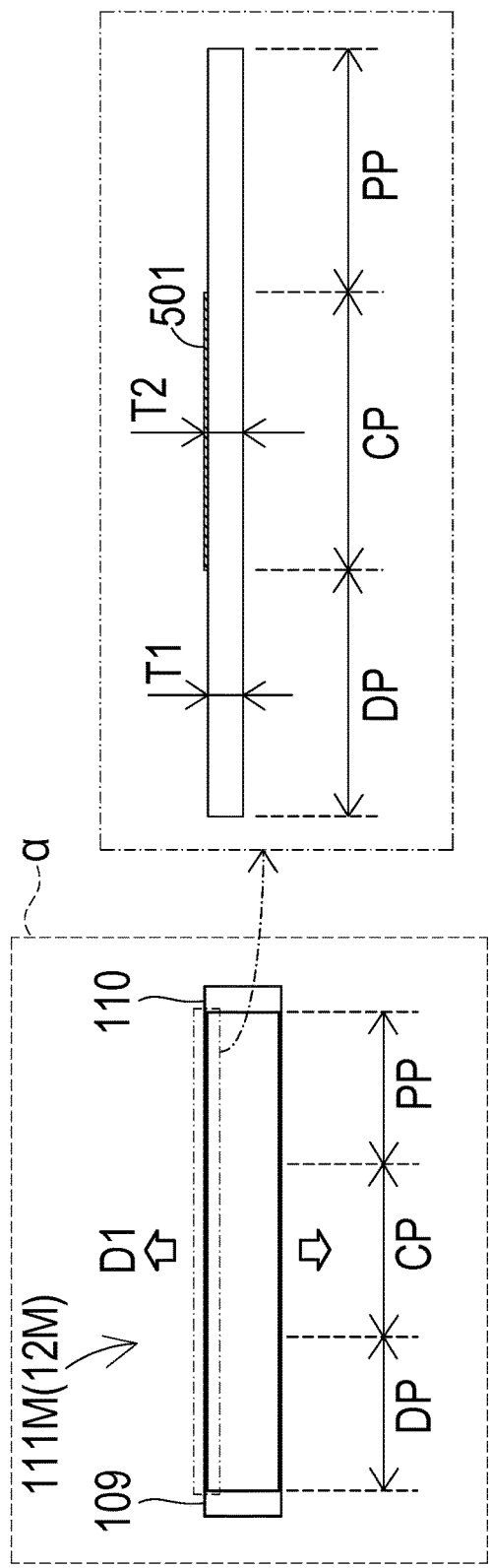
FIGS. 14A and 14B are explanatory diagrams illustrating configurations of an expansion/contraction portion according to a sixth aspect of the disclosed embodiments.
Figure 14B:
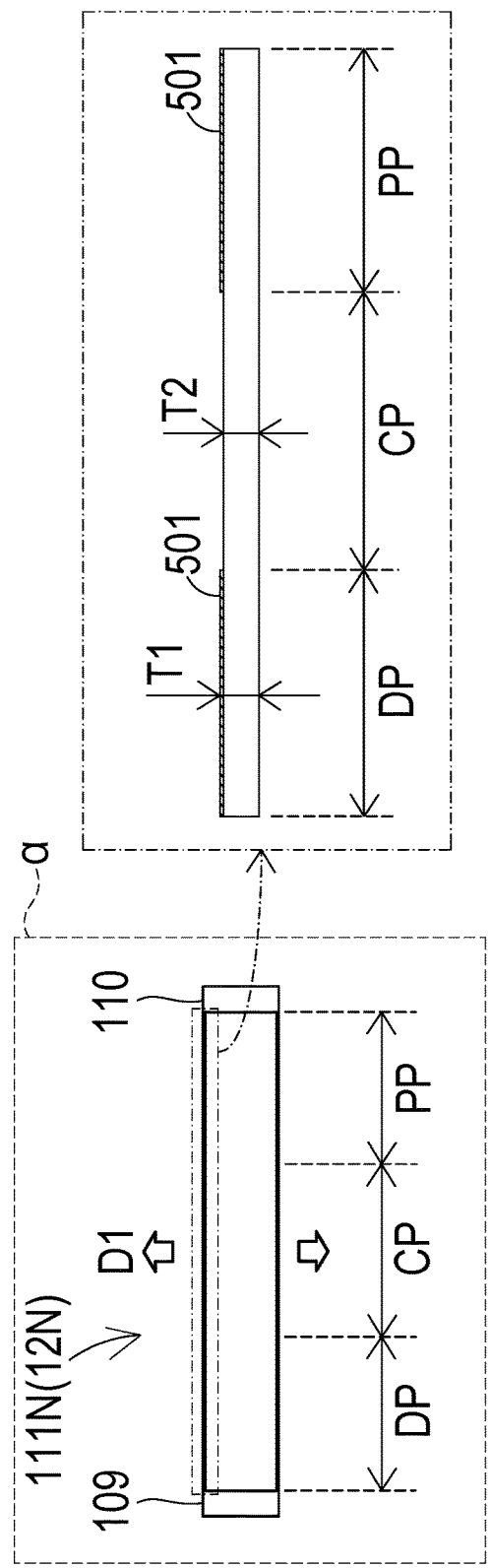

FIGS. 14A and 14B are explanatory diagrams illustrating configurations of expansion/contraction portions 12M and N according to a sixth aspect of the disclosed embodiments. FIG. 14A illustrates an example of the configuration of the expansion/contraction portion 12M, and FIG. 14B illustrates an example of the configuration of the expansion/contraction portion 12N.

Regarding the expansion/contraction portions 12M and 12N according to the sixth aspect of the disclosed embodiments, in suspension portions 111M and 111N, a rigidity of a central portion CP is made different from rigidities of a distal end portion DP and a proximal end portion PP by a method different from that in the second aspect of the disclosed embodiments.

Specifically, in the example of FIG. 14A, in the suspension portion 111M, a plating layer 501 is formed on a side face of the central portion CP in the expansion direction D1, meanwhile the distal end portion DP and the proximal end portion PP have no plating layer. The plating layer 501 is a thin film made of a metal material such as gold and platinum.

In such a way, a thickness T2 of the central portion CP can be made larger than thicknesses T1 of the distal end portion DP and the proximal end portion PP by the formed plating layer 501, so that the rigidity of the central portion CP can be made higher than the rigidities of the distal end portion DP and the proximal end portion PP. Additionally, in the example of FIG. 14B, in the suspension portion 111N, the plating layer 501 is formed on side faces of the distal end portion DP and the proximal end portion PP in the expansion direction D1, meanwhile the central portion CP has no plating layer. In such a way, the rigidity of the central portion CP can be made lower than the rigidities of the distal end portion DP and the proximal end portion PP. Incidentally, it is sufficient that the plating layer 501 is formed on side faces of the distal end portion DP and the proximal end portion PP in the expansion direction D1. Thus, as illustrated in the figure, the plating layer 501 may be formed outside (on a radially outer side) in the expansion direction D1, or inside (on a radially inner side) in the expansion direction D1 (opposite to the side illustrated in FIGS. 14A and 14B).

As in the sixth aspect of the disclosed embodiments, the rigidity of the central portion CP may be made different from the rigidities of the distal end portion DP and the proximal end portion PP by adopting the layered configuration e.g. the plating layer 501 formed on either the central portion CP or the distal end portion DP and the proximal end portion PP of the suspension portion 111M and 111N. Also in such a way, the same effect as of the second aspect of the disclosed embodiments can be exhibited. Additionally, in the suspension portions 111M and 111N according to the sixth aspect of the disclosed embodiments, antibacterial and bacteriostatic effects can be provided to the surfaces of the suspension portions 111M and 111N, or water repellency can be provided on the surfaces of the suspension portions 111M and 111N by changing a material of the plating layer 501.

G. Seventh Aspect

Figure 15A:
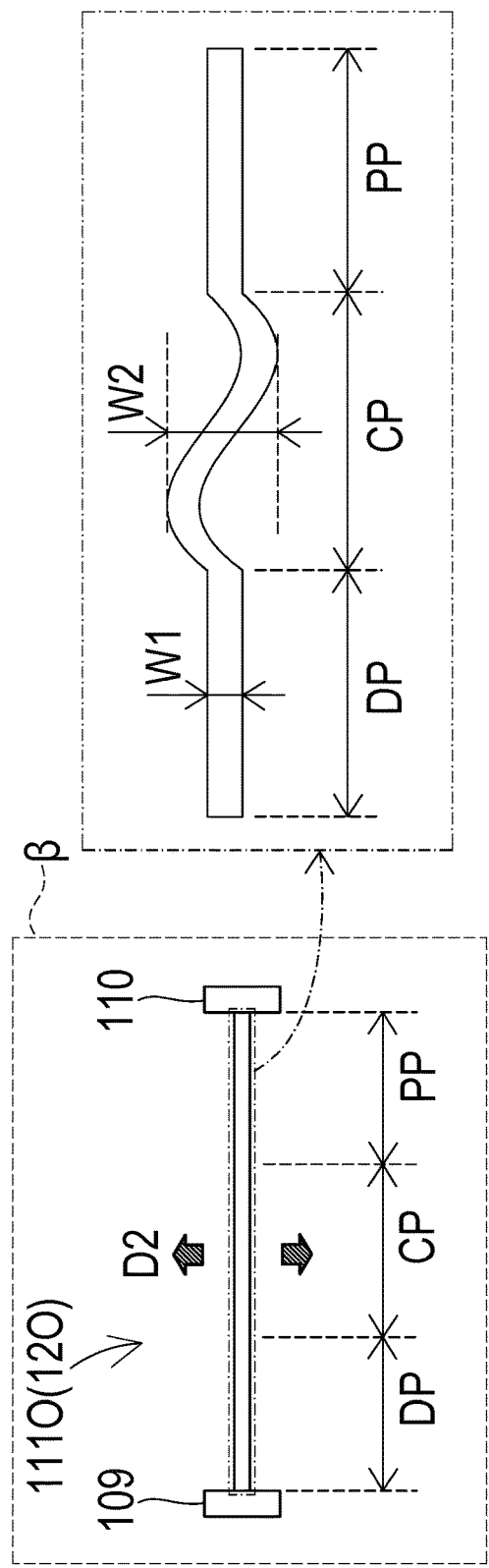
FIGS. 15A and 15B are explanatory diagrams illustrating configurations of an expansion/contraction portion according to a seventh aspect of the disclosed embodiments.
Figure 15B:
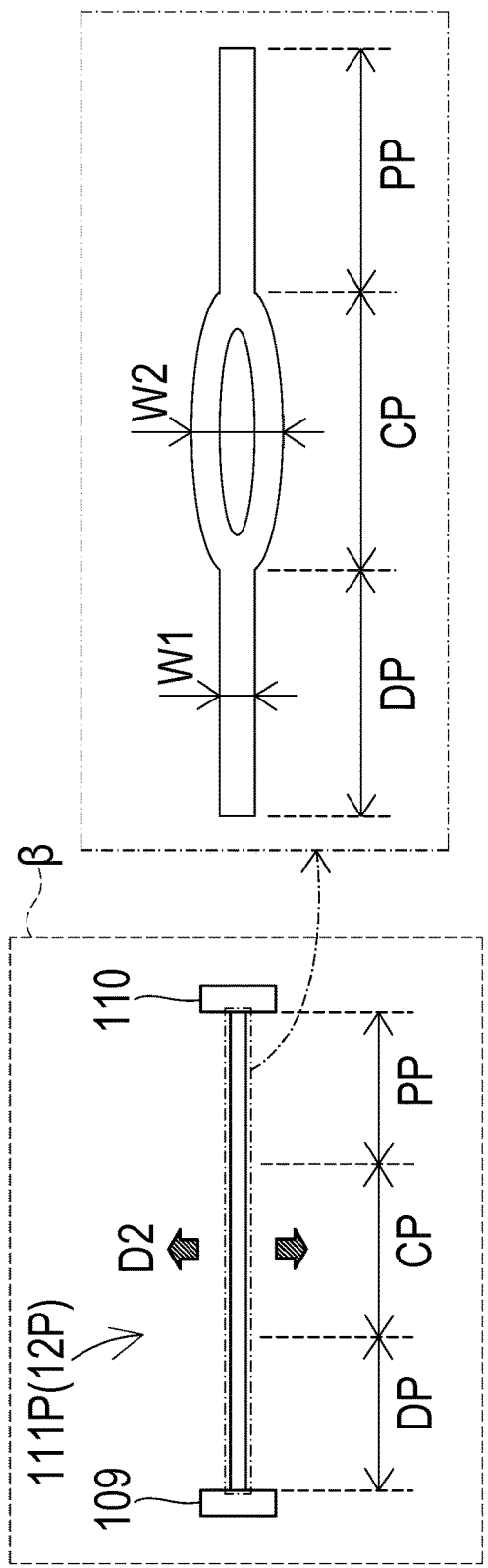

15A and 15B are explanatory diagrams illustrating configurations of expansion/contraction portions 12O and 12P according to a seventh aspect of the disclosed embodiments. FIG. 15A illustrates an example of the configuration of the expansion/contraction portion 12O, and FIG. 15B illustrates an example of the configuration of the expansion/contraction portion 12P. Regarding the expansion/contraction portions 12O and 12P according to the seventh aspect of the disclosed embodiments, in suspension portions 111O and 111P, a rigidity of a central portion CP is made different from rigidities of a distal end portion DP and a proximal end portion PP by a method different from that in the second aspect of the disclosed embodiments.

Specifically, in the example of FIG. 15A, in the suspension portion 111O, the distal end portion DP and the proximal end portion PP have a straight shape linearly extending in the longitudinal direction, meanwhile the central portion CP has a curved shape widely waving in the orthogonal direction D2. In the orthogonal direction D2, the width W2 from an upper end to a lower end of the central portion CP is wider than widths W1 of the distal end portion DP and the proximal end portion PP. In such a way, the rigidity of the central portion CP can be made higher than the rigidities of the distal end portion DP and the proximal end portion PP. Additionally, in the example of FIG. 15B, in the suspension portion 111P, the distal end portion DP and the proximal end portion PP have a straight shape linearly extending in the longitudinal direction, meanwhile the central portion CP has a hollow elliptical shape widely branching out in the orthogonal direction D2. In the orthogonal direction D2, the width W2 from the upper end to the lower end of the central portion CP is larger than the widths W1 of the distal end portion DP and the proximal end portion PP. Also in such a way, the rigidity of the central portion CP can be made higher than the rigidities of the distal end portion DP and the proximal end portion PP. Incidentally, the shape of the central portion CP is not limited to the curved shape or the hollow elliptical shape, and can be arbitrarily changed to an arc, circle, rectangle, trapezoid, other polygonal shapes, or the like.

The rigidity of the central portion CP may be made different from the rigidities of the distal end portion DP and the proximal end portion PP by changing the shape of the central portion CP and/or the shapes of the distal end portion DP and the proximal end portion PP in the suspension portions 111O and 111P as in the seventh aspect of the disclosed embodiments. Also in such a way, the same effect as of the second aspect of the disclosed embodiments can be exhibited. Additionally, in the suspension portions 111O and 111P in the seventh aspect of the disclosed embodiments, a structure of the suspension portions 111O and 111P that is easily laser-processed can be obtained by making the difference in rigidity depending on the widths W1 and W2 in the orthogonal direction D2.

H. Eighth Aspect

Figure 16:
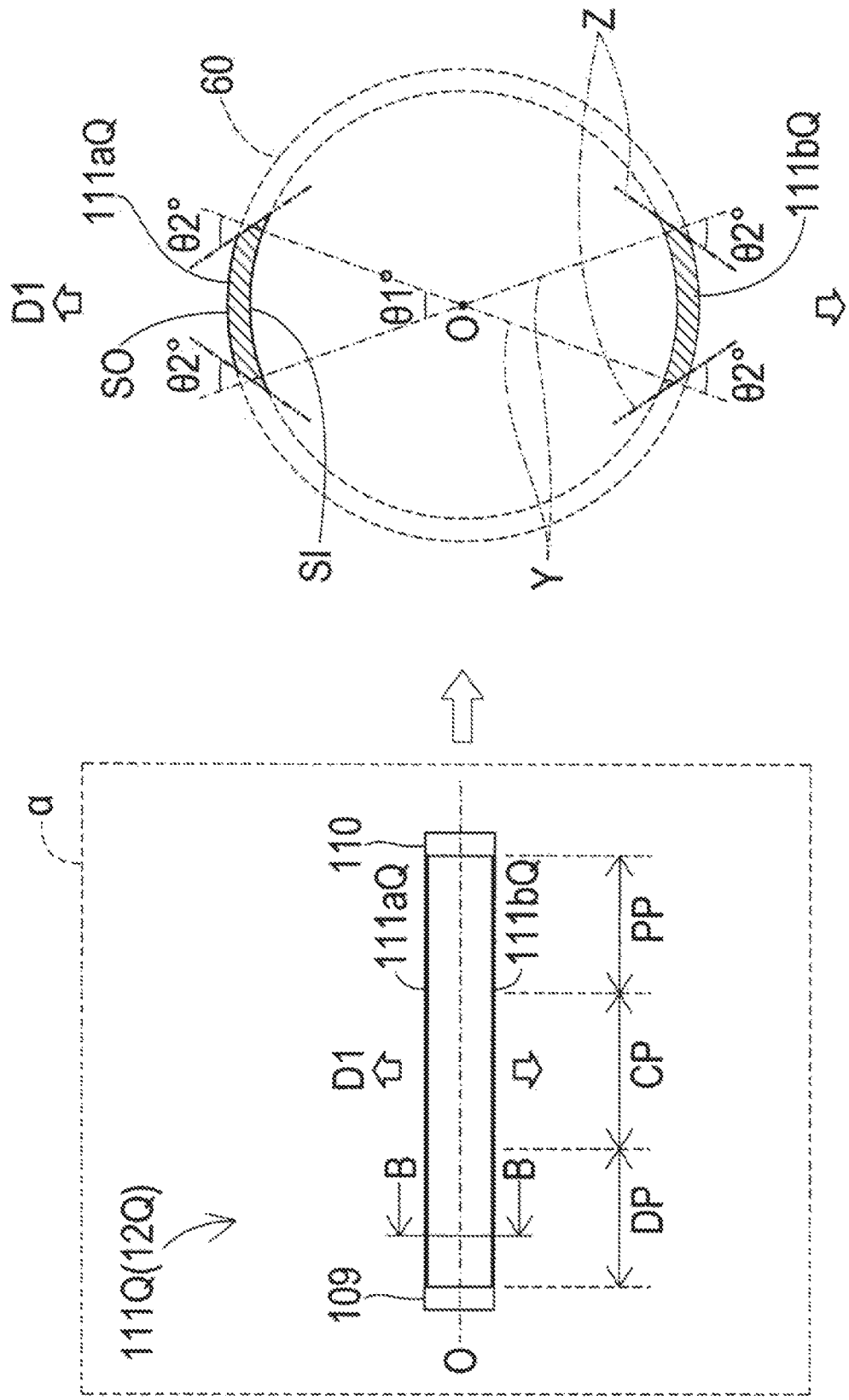
FIG. 16 is an explanatory diagram illustrating a configuration of an expansion/contraction portion according to an eighth aspect of the disclosed embodiments.

FIG. 16 is an explanatory diagram illustrating a configuration of an expansion/contraction portion 12Q according to an eighth aspect of the disclosed embodiments. On the left side of FIG. 16, the contracted (not expanded) expansion/contraction portion 12Q on the virtual plane α is illustrated, and on the right side, a sectional view of a suspension portion 111Q taken along line B-B of the left figure is illustrated. The expansion/contraction portion 12Q according to the eighth aspect of the disclosed embodiments has the expansion/contraction portion 12Q having a different configuration from the first aspect of the disclosed embodiments. As illustrated in the right figure, the suspension portion 111Q of the expansion/contraction portion 12Q is composed of a first suspension portion 111*a*Q and a second suspension portion 111*b*Q that have a cross-sectional shape obtained by curving a rectangular shape so as to protrude toward the expansion direction D1 outside the first inner shaft 102 in the radial direction. In other words, each of the first suspension portion 111*a*Q and the second suspension portion 111*b*Q of the suspension portion 111Q has two sides SO and SI along the circumferential direction, in which a length of the side SI closer to the first inner shaft 102 is formed so as to be longer than a length of the side SO farther from the first inner shaft 102.

The expansion/contraction portion 12Q according to the eighth aspect of the disclosed embodiments is formed by cutting out the cylindrical hollow pipe 60 (dashed line) explained in FIGS. 2D to F on virtual planes Z described below. First, in the cross-sectional view in the figure, two virtual planes that intersect with each other at a center O of the hollow pipe at θ1° are defined as virtual planes Y (dot and dash line). Next, four virtual planes that intersect with the two virtual planes Y at θ2° on the wall portion of the hollow pipe 60 are defined as the virtual planes Z (two-dot and dash line). Herein, θ1° and θ2° may be arbitrarily determined.

As in the eighth aspect of the disclosed embodiments, the configuration of the suspension portion 111Q can be variously changed, and can also be modified by a means other than difference in the rigidities between the central portion CP and the distal and proximal end portions DP and PP. Also in such a way, the same effect as of the first aspect of the disclosed embodiments can be exhibited. In addition, since the cross-sectional shape of the suspension portion 111Q according to the eighth aspect of the disclosed embodiments is a shape obtained by curving a rectangular shape so as to protrude (curve) outward in the radial direction of the first inner shaft 102 (shaft), hooking of the suspension portion 111Q can be suppressed by slidingly moving a distal end face of the protrusion on the living tissue when the catheter is turned in the circumferential direction, and injury of the living tissue due to the suspension portion 111Q can be suppressed.

I. Ninth Aspect

Figure 17A:
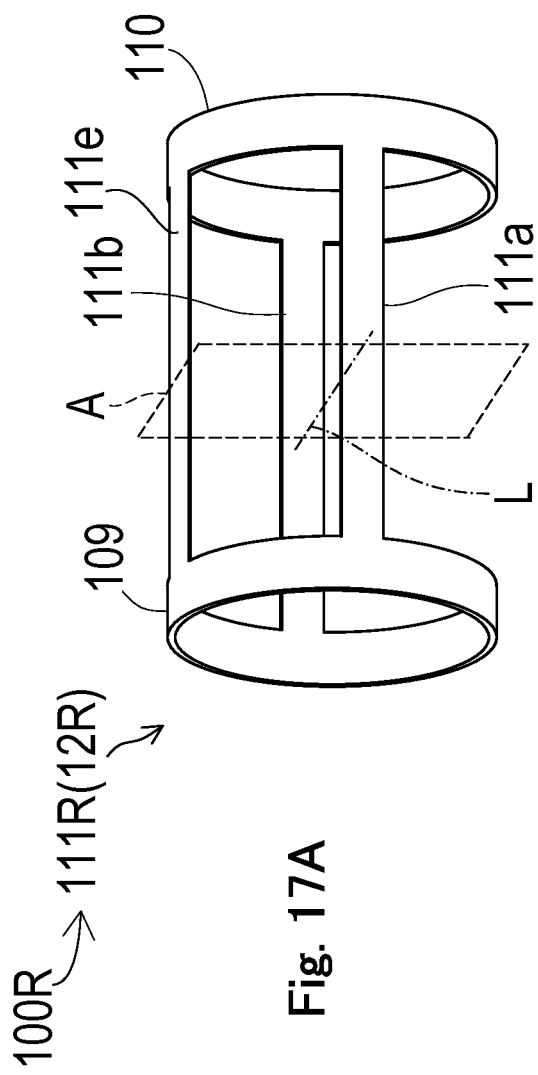
FIGS. 17A and 17B are explanatory diagrams illustrating configurations of an expansion/contraction portion according to a ninth aspect of the disclosed embodiments.
Figure 17B:
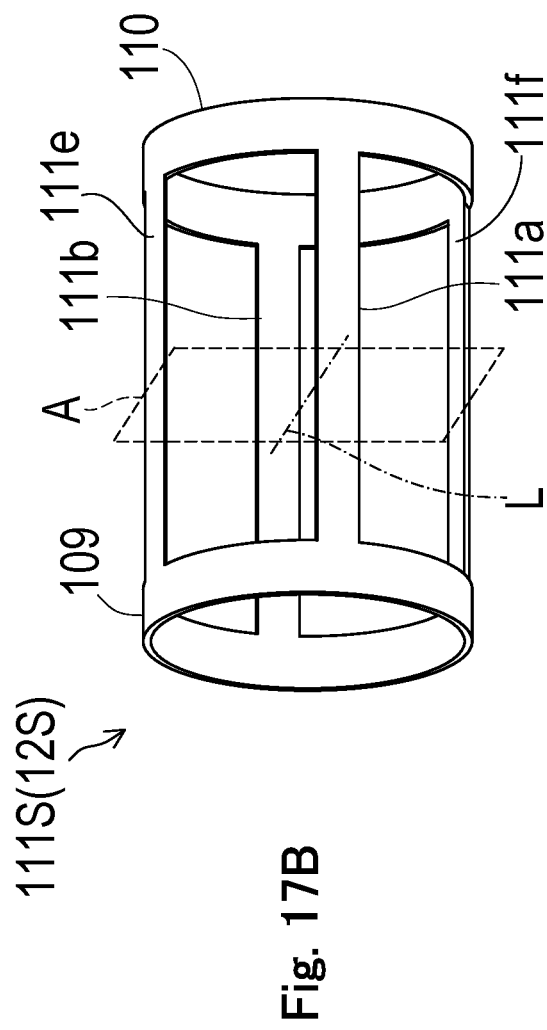

FIGS. 17A and 17B are explanatory diagrams illustrating configurations of expansion/contraction portions 12R and S according to a ninth aspect of the disclosed embodiments. FIG. 17A illustrates an example of the expansion/contraction portion 12R, and FIG. 17B illustrates an example of the expansion/contraction portion 12S. The expansion/contraction portions 12R and S have suspension portions 111R and 111S respectively instead of the suspension portion 111 explained in the first aspect of the disclosed embodiments.

The suspension portion 111R illustrated in FIG. 17A further includes a third suspension portion 111e in addition to the first and second suspension portions 111a and 111b explained in the first aspect of the disclosed embodiments. On a cross section A of the suspension portion 111R indicated by a dashed line, the first and second suspension portions 111a and 111b are opposite to each other. Herein, on the cross section A, a virtual line L (dot and dash line) connecting each center of the first and second suspension portions 111a and 111b is defined. The third suspension portion 111e is disposed in one of two regions (referred to as "upper region" and "lower region" for convenience) with the virtual line L as a boundary. Specifically, in the example in the figure, the third suspension portion 111e is disposed in the upper region and at a position from which the distances to the first and second suspension portions 111a and 111b are substantially the same on the cross section A. In such a way, the suspension portion 111R can functionally act as an orientation marker with higher accuracy for confirming a posture and an orientation of the catheter 100R on an image from the imaging sensor 200.

The suspension portion 111S illustrated in FIG. 17B further includes a fourth suspension portion 111f in addition to the aforementioned third suspension portion 111e. The fourth suspension portion 111f is disposed in the other one of the two regions with the virtual line L as a boundary. Specifically, in the example in the figure, the fourth suspension portion 111f is disposed in the lower region and at a position from which the distances to the first and second suspension portions 111a and b are substantially the same on the cross section A. In such a way, a number of the suspension portions disposed on the suspension portion 111S can be arbitrarily determined, and may be one, or three or more. Also in such a way, the same effect as of the first aspect of the disclosed embodiments can be exhibited.

J. Tenth Aspect

Figure 18A:
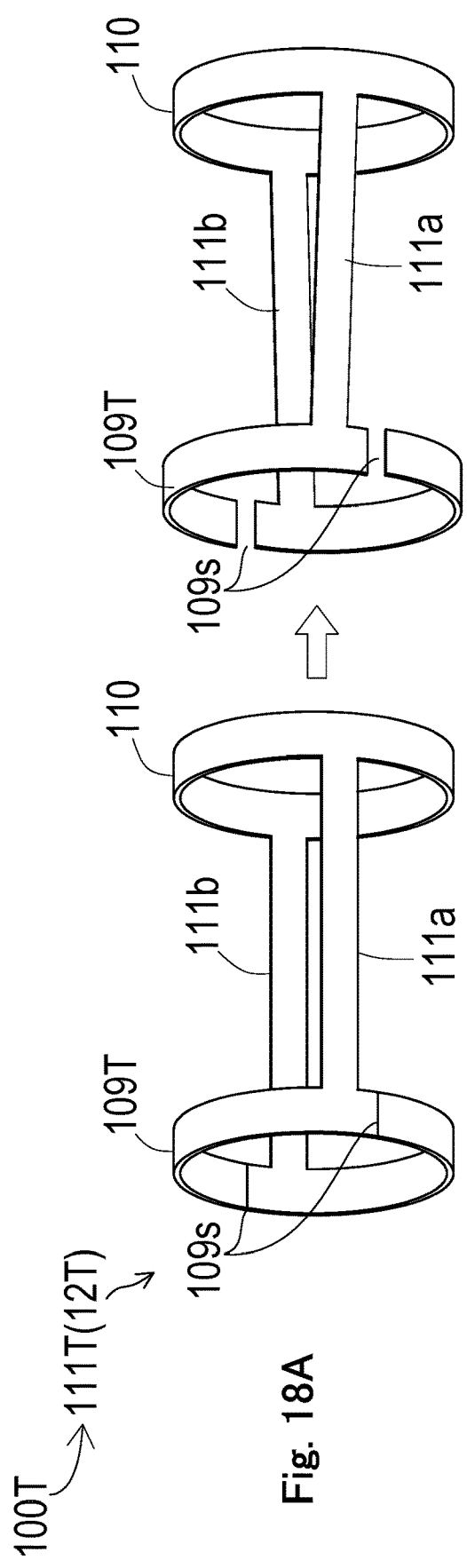
FIGS. 18A and 18B are explanatory diagrams illustrating configurations of an expansion/contraction portion according to a tenth aspect of the disclosed embodiments.
Figure 18B:
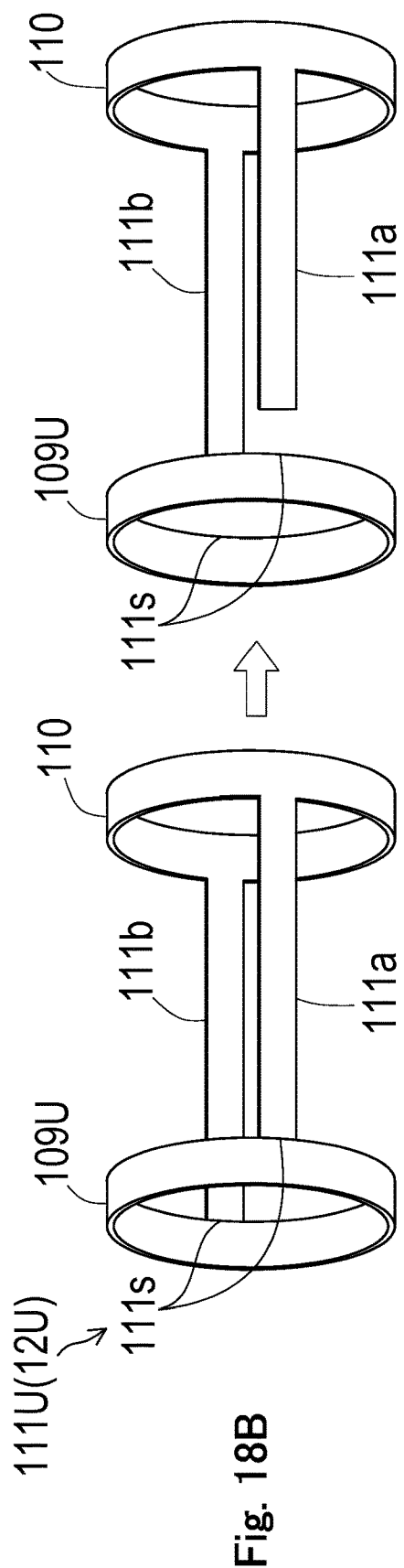

FIGS. 18A and 18B are explanatory diagrams illustrating configurations of expansion/contraction portions 12T and 12U according to a tenth aspect of the disclosed embodiments. FIG. 18A illustrates an example of the expansion/contraction portion 12T, and FIG. 18B illustrates an example of the expansion/contraction portion 12U. The expansion/contraction portions 12T and 12U have suspension portions 111T and 111U respectively instead of the suspension portion 111 explained in the first aspect of the disclosed embodiments.

The suspension portion 111T illustrated in FIG. 18A includes a fixed portion 109T instead of the fixed portion 109 explained in the first aspect of the disclosed embodiments. The fixed portion 109T has two separable portions 109s disposed in a longitudinal direction of a catheter 100T. During the procedure explained in in FIGS. 5A-5D, there is a possibility that the catheter 100T cannot be moved in the coronary artery 80 when the suspension portion 111T is hooked by calcified tissues of CTO 81, the stent placed in the blood vessel, or the like. In such a case, the separable portions 109s are configured such that the catheter 100T can be retrieved by separating the suspension portion 111T as illustrated on the right side in FIG. 18A. The separable portions 109s can be configured as notches (slit) formed in a wall portion of the fixed portion 109T. Also, the separable portions 109s may be configured to be brittle by thinning a part of the fixed portion 109T, or by forming through-holes, or by changing the material.

If the suspension portion 111T is hooked, the operator operates the first dial 105a (FIG. 1) of the regulator 105 of the catheter 100T to pull the first and second wires 112a and 112b toward the proximal end side. Thereby, as illustrated on the right side in FIG. 18A, the separable portions 109s can be ruptured, so that the fixed portion 109T can be separated. As a result, the operator can easily retrieve the catheter 100T. In addition, since each ruptured fixed portion 109T can be associated with the first and second suspension portions 111a and 111b by disposing each of the separable portions 109s as illustrated in the figure, the ruptured fixed portions 109T can be prevented from remaining in the body.

In the suspension portion 111U illustrated in FIG. 18B, two separable portions 111s are formed on a boundary between a fixed portion 109U and the first and second suspension portions 111a and 111b. In addition, the fixed portion 109U is joined to the surface of the first inner shaft 102 by pressure bonding or with an adhesive or the like. The separable portions 111s can be formed by notches or embrittlement similarly to the separable portions 109s. If the suspension portion 111U is hooked, the operator pulls the first and second wires 112a and 112b toward the proximal end side like FIG. 18A. Thereby, as illustrated on the right side in FIG. 18B, the separable portions 111s can be ruptured, so that the fixed portion 109U can be separated. In addition, since the fixed portion 109U is joined to the surface of the first inner shaft 102, the ruptured fixed portions 109U can be prevented from remaining in the body.

As described above, configurations of the expansion/contraction portions 12T and 12U can be variously changed, and another configuration not explained in the first aspect of the disclosed embodiments may be provided. Also in such a way, the same effect as of the first aspect of the disclosed embodiments can be exhibited. In addition, even if the catheters 100T and 100U cannot be moved in the coronary artery 80, the catheters 100T and 100U can be easily retrieved by the expansion/contraction portions 12T and 12U according to the tenth aspect of the disclosed embodiments.

K. Eleventh Aspect

Figure 19:
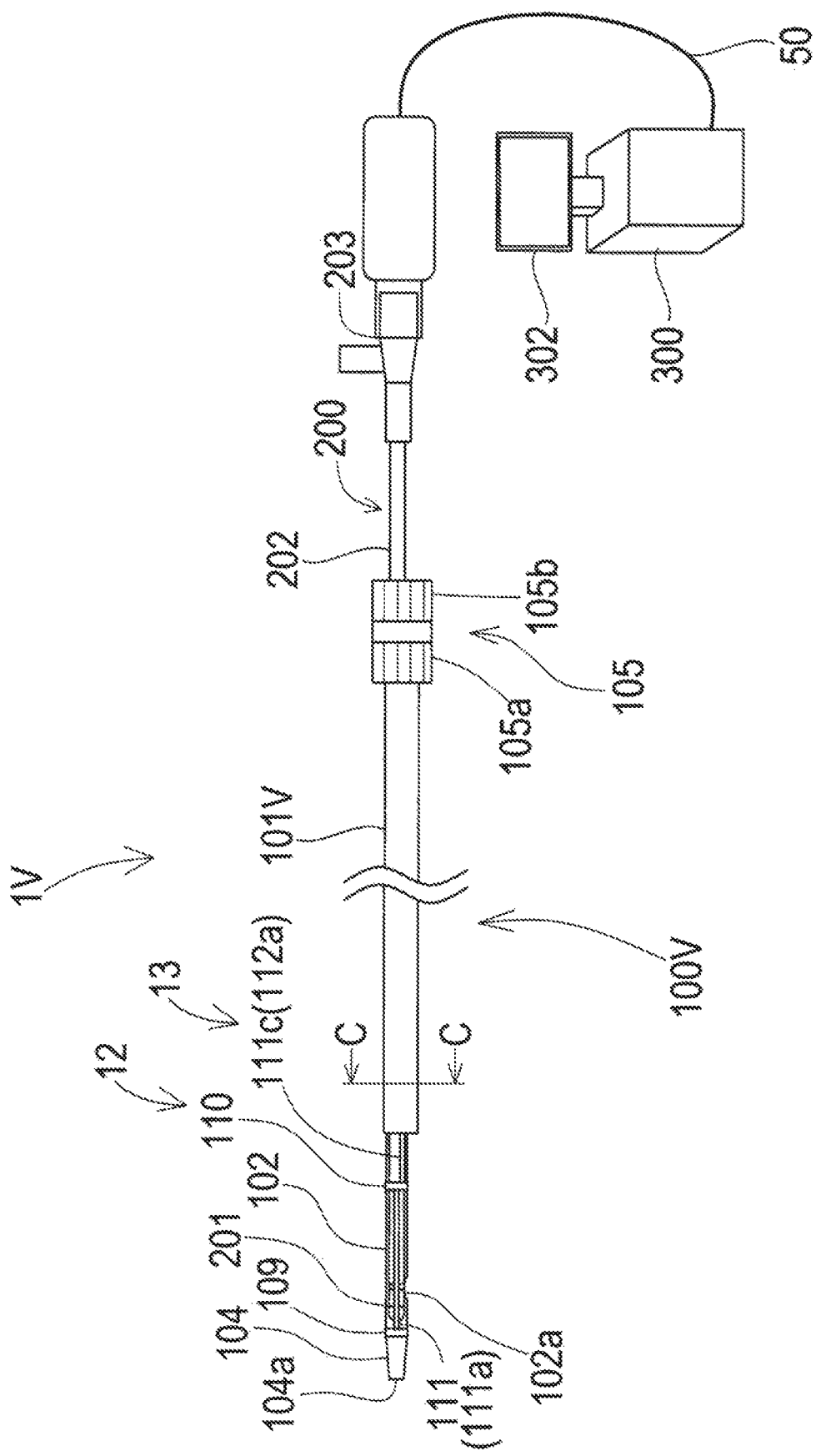
FIG. 19 is a schematic diagram illustrating an entire configuration of a recanalization catheter system according to an eleventh aspect of the disclosed embodiments.
Figure 20:
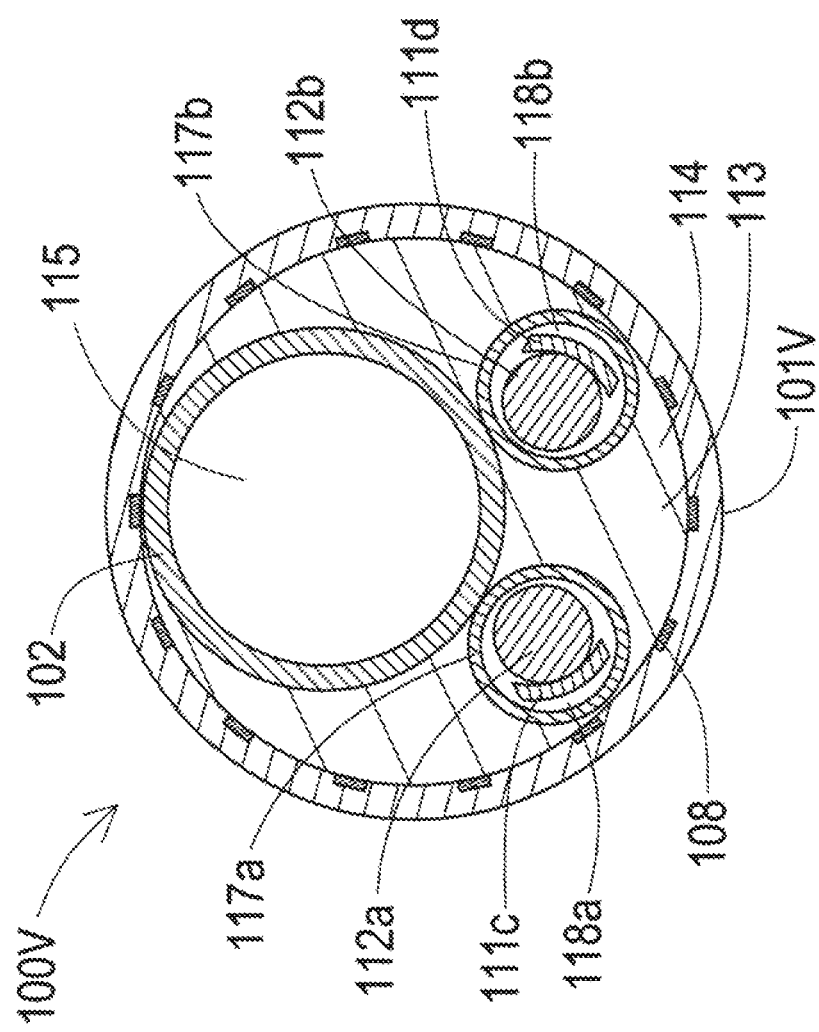
FIG. 20 is a schematic sectional view of the catheter taken along line C-C in FIG. 19.

FIG. 19 is a schematic diagram illustrating an entire configuration of a recanalization catheter system 1V according to an eleventh aspect of the disclosed embodiments. FIG. 20 is a schematic sectional view of a catheter 100V taken along C-C line in FIG. 19. The recanalization catheter system 1V according to the eleventh aspect of the disclosed embodiments includes the catheter 100V instead of the catheter 100 explained in the first aspect of the disclosed embodiments. Incidentally, in FIG. 19, illustration of the penetration guide wire 400 is omitted for convenience of illustration. As illustrated in FIG. 20, the catheter 100V does not include the second inner shaft 103 explained in the first aspect of the disclosed embodiments but an outer shaft 101V to which the first inner shaft 102 is inserted. Thus, the catheter 100V does not have the second lumen 116 and the opening 103a formed by the second inner shaft 103, and a configuration with only the first lumen 115 is used for inserting the medical device.

With the recanalization catheter system 1V according to the eleventh aspect of the disclosed embodiments, CTO can be canalized as described below. First, the delivery guide wire 70 is previously inserted into the coronary artery 80 (see FIG. 5A), and in this state, the proximal end of the delivery guide wire 70 is inserted from the opening 104a, passed through the lumen inside the distal tip 104 and the first lumen 115 of the first inner shaft 102 (see FIG. 20), and protruded outward from the opening 102a of the first inner shaft 102. Then, the catheter 100V is transported to the false cavity 82 along the delivery guide wire 70. At this time, the catheter 100 is transported such that the imaging sensor 200 is inserted into the first lumen 115. While confirming an image of the coronary artery 80 from the imaging sensor 200 inserted into the first lumen 115, the operator disposes the catheter 100V at an optimum position for penetration into the true cavity with the penetration guide wire 400. After disposing the catheter 100V at the optimum position, the operator turns the catheter 100V on the basis of the position of the delivery guide wire 70 on the image from the imaging sensor 200 as an indicator.

Subsequently, the operator operates the first dial 105a to expand the suspension portion 111 of the expansion/contraction portion 12. The catheter 100V is fixed inside the false cavity 82 by expansion of the suspension portion 111. Then the operator removes the delivery guide wire 70 and the imaging sensor 200, and newly inserts a penetration guide wire 400 into the first lumen 115. The operator transports the pointed portion of the penetration guide wire 400 to the distal end portion of the catheter 100V, and protrudes the pointed portion of the penetration guide wire 400 outward from the opening 102a or the opening 104a. Herein, when the optimum site for penetration is near the distal end portion of the catheter 100V, it is preferable that the penetration guide wire 400 protrudes from the opening 104a. On the other hand, when the optimum site for penetration is near the side face of the catheter 100V, it is preferable that the penetration guide wire 400 protrudes from the opening 102a. Subsequently, the operator penetrates the living tissue using the pointed portion of the penetration guide wire 400 and makes the distal end of the penetration guide wire 400 reach the true cavity 84.

In such a way, the configuration of the catheter 100V can be variously changed, and for example, a number of lumens for inserting a medical device may be one, or three or more. In the recanalization catheter system 1V according to the eleventh aspect of the disclosed embodiments, the catheter 100V includes one first lumen 115 (lumen, FIG. 20) for inserting the medical device, and therefore the diameter of the catheter 100V can be decreased. In addition, since the distal end portion of the shaft includes the first inner shaft 102 whose distal end portion extends to the distal end side of the distal end portion of the outer shaft 101V, the inside of the false cavity 82 can be observed with higher accuracy by inserting the imaging sensor 200 (sensor) into the first lumen 115 and disposing the transducer 201 of the imaging sensor 200 on the first lumen 115 in the first inner shaft 102. Furthermore, since the catheter 100V includes the expansion/contraction portion 12 that is expandable and contractible in the radial direction, the catheter 100V is positioned by advancing/retracting and turning the catheter 100V, and then the suspension portion 111 is expanded, where the catheter 100V can be fixed.

In addition, the catheter 100V according to the eleventh aspect of the disclosed embodiments includes the opening 104a communicating with the first lumen 115 (lumen) on the distal end portion of the first inner shaft 102 extending to the distal end side of the distal end portion of the outer shaft 101V, and the opening 102a (first opening) communicating with the first lumen 115 on the side face of the proximal end side of the opening 104a. Thereby, the proximal end side of the delivery guide wire 70 can be inserted into the first lumen 115 from the opening 104a and passed through the first lumen 115, and furthermore the proximal end side of the delivery guide wire 70 can be protruded outward from the opening 102a (first opening). Thereby, the catheter 100V can also be used as a rapid exchange-type catheter, and therefore diversity of the procedure can be widened and usability can be improved. In addition, when the penetration guide wire 400 is used while inserted into the first lumen 115, penetration of the living tissue positioned near the distal end portion of the catheter 100V can be facilitated by protruding the pointed portion of the penetration guide wire 400 outward from the opening 104a. Furthermore, penetration of the living tissue positioned near the side face of the catheter 100V can be facilitated by protruding the pointed portion of the penetration guide wire 400 outward from the opening 102a.

L. Modification Example

Note that the disclosed embodiments are not limited to the above aspects, and can be implemented in various other aspects without departing from the gist of the disclosed embodiments. For example, the following modifications are also possible.

Modification Example 1

In the first to eleventh aspects of the disclosed embodiments, some examples of the configurations of the recanalization catheter systems 1 and 1V have been described. However, the configurations of the recanalization catheter systems 1 and 1V can be variously changed. For example, as the imaging sensor 200, a sensor acquiring an image of the living tissue with another means other than transmission and reception of ultrasonic waves may be used. Also, instead of the imaging sensor 200, an OCT (Optical Coherence Tomography) or a camera can be inserted into the lumen to acquire an image of the living tissue inside the blood vessel. When adopting the OCT or the camera, it is necessary to inject physiological saline or the like into the first lumen 115.

For example, a system for canalizing the CTO using a plasma guide wire that ablates the living tissue utilizing a plasma without using the penetration guide wire 400 may be configured. In this case, it is preferable that, in the catheter 100, 100A, 100B, 100R, 100T, and 100V, the braid 108 is made of a conductive metal material, and then an electrode electrically connected to the braid 108 is disposed on the distal end side of the outer shaft 101. Thereby the plasma guide wire can be used by connecting the electrode disposed on the distal end side of the outer shaft 101 and the proximal end side of the braid 108 to an RF generator.

Modification Example 2

In the first to eleventh aspects of the disclosed embodiments, some examples of methods of using the recanalization catheter systems 1 and 1V have been described. However, the recanalization catheter systems 1 and 1V may be used in another method not described above. For example, the recanalization catheter system may be used for a blood vessel other than the coronary artery (e.g. cerebral vessel or the like), or may be used in a living body lumen other than blood vessels. For example, the recanalization catheter system may be used for treatments and tests other than the CTO recanalization.

Modification Example 3

In the first to eleventh aspects of the disclosed embodiments, some examples of the configurations of the catheters 100, 100A, 100B, 100R, 100T, and 100V have been described. However, the configurations of the catheters 100, 100A, 100B, 100R, 100T, and 100V can be variously changed. For example, in the catheter, the first lumen 115 and the second lumen 116 may have substantially the same diameter, or structurally the first lumen may have a smaller diameter than of the second lumen. For example, the catheter may include not only the first lumen and the second lumen but also another lumen for a medical device such as a penetration guide wire.

For example, the opening 104a communicating with the first lumen 115 may be formed at a position other than the distal end face of the distal tip 104 (e.g. side face of the distal tip 104, or the like). Similarly, the opening 102a communicating with the first lumen 115 may be formed at a position other than the side face opposite to the second lumen 116 in the first inner shaft 102. Similarly, the opening 103a communicating with the second lumen 116 may be formed at a position other than the distal end face of the first inner shaft 102 (e.g. side face of the second inner shaft 103, or the like). For example, at least one or some of the opening 104a, the opening 102a, and the opening 103a may be omitted. Another opening not illustrated may be formed. The other opening can be exemplified by an opening communicating with the second lumen 116 e.g. on the side face of the outer shaft 101.

For example, in the first inner shaft 102, a part extending to the distal end side of the distal end portion of the second lumen 116 is preferably made of a polyamide from the viewpoint of achieving both the ultrasonic transmittance and securement of the wall thickness of the imaging sensor 200. On the other hand, in the first inner shaft 102, a part extending to the proximal end side of the distal end portion of the second lumen 116, as well as the outer shaft 101, the second inner shaft 103, the sealing member 114, and the like is preferably made of a polytetrafluoroethylene (PTFE), a polyimide, a copolymer of tetrafluoroethylene and perfluoroalkoxyethylene (PFA), or the like, from the viewpoint of securing rigidity. In addition, the distal tip 104 is preferably made of polyurethane from the viewpoint of securing flexibility.

In the first inner shaft 102, a wall thickness of a part extending to the proximal end side of the distal end portion of the second lumen 116 is preferably 20 micron or larger for insulation from the conductive braid 108. The distal end of the second inner shaft 103 does not slope toward the first inner shaft 102 and may have a flat distal end face. For example, the catheter may include, instead of the braid 108, a coil body made of a conductive metal material as a reinforcing member. Alternatively, the catheter may include both the braid 108 and the coil body. For example, the suspension portion 111 may be coated with a conductive resin, or may have a surface applied with an agent.

Modification Example 4

In the first to eleventh aspects of the disclosed embodiments, some examples of the configurations of the expansion/contraction portions 12, 12A to 12U, and the actuation portion 13 have been explained. However, the configurations of the expansion/contraction portions 12, 12A to 12U, and the actuation portion 13 can be variously changed. For example, the suspension portion 111 of the expansion/contraction portion 12 may be made of a mesh member made of a metal material or a resin material instead of the plate-like member. For example, a balloon for covering the suspension portion 111 of the expansion/contraction portion 12 may be further provided. In this case, the outer shaft 101 may further include a hollow inflation shaft connected to the balloon to feed a working fluid to the balloon. The configuration with the balloon makes it possible to confirm opening or closing of the suspension portion 111 under an X-ray image by injecting the working fluid containing an X-ray impermeable material to the balloon through the inflation shaft.

For example, the suspension portion 111 of the expansion/contraction portion 12 may be made of a member having a large difference in an acoustic impedance from the living tissue. Furthermore, concave and convex structures may be formed on the surface of the suspension portion 111 to enhance reflection of the ultrasonic wave from the transducer 201 of the imaging sensor 200. Thereby the suspension portion 111 can functionally act as an orientation marker for confirming the posture and orientation of the catheter 100 on the image acquired by the imaging sensor 200. Incidentally, at this time, the suspension portion 111 may be opened or closed.

For example, in the suspension portion 111 of the expansion/contraction portion 12, the rigidity of the central portion CP may be equivalent to the rigidities of the distal end portion DP and the proximal end portion PP. In addition, even when the rigidity of the central portion CP is made relatively different from the rigidities of the distal end portion DP and the proximal end portion PP, the rigidities may be made different from each other by using a method other than the methods explained in the second to tenth aspects of the disclosed embodiments. For example, the rigidities may be made different by using different materials between the central portion CP and the distal end and proximal end portions DP and PP. For example, in the expansion/contraction portion 12, the fixed portion 109 is disposed on the distal end side of the sliding portion 110. However, the fixed portion 109 may be disposed on the proximal end side of the sliding portion 110. For example, in the suspension portion 111 of the expansion/contraction portion 12, the longitudinal lengths of the central portion CP, the distal end portion DP, and the proximal end portion PP may be the same or different from each other. In addition, the length of the central portion CP in the longitudinal direction may be shorter than the lengths of the distal end portion DP and the proximal end portion PP in the longitudinal direction.

For example, the shape of the expanded suspension portion 111 (opened shape viewed from the bottom side) is not necessarily substantially trapezoid. Specifically, for example, the shape of the expanded suspension portion 111 may be an arc shape such that the distances of the first and second suspension portion 111a and 111b away from the outer peripheral face of the first inner shaft 102 gradually increase from the distal end and the proximal end toward the center. In addition, the expanded suspension portion 111 may be a distorted arc shape such that a point farthest from the first inner shaft 102 is biased toward one of the distal end side and the proximal end side. For example, the shape of the expanded suspension portion 111 may also be a rectangle or polygon.

For example, the actuation portion 13 may be configured to utilize a pressing force of a fluid without using the first wire 112a and the second wire 112b. In this case, a balloon is attached to the first inner shaft 102, and the proximal end of the sliding portion 110 is attached to the distal end of the balloon. The balloon is expanded by feeding the working fluid into the balloon. The sliding portion 110 is moved to the distal end side by the pressing force of the expanded balloon, so that the suspension portion 111 can be expanded. In addition, the balloon is contracted by discharging the working fluid in the balloon, and the sliding portion 110 is moved to the proximal end side, so that the suspension portion 111 can be contracted.

For example, the suspension portion 111 of the expansion/contraction portion 12 may be a suspension portion to which an expanded shape has been memorized (hereinafter referred to as "suspension portion 111M"). In this case, the actuation portion 13 is configured to include a hollow cylindrical outer sheath instead of the first wire piece 111c and the second wire piece 111d and the first and second wires 112a and 112b. The outer sheath is disposed so as to cover the outer periphery of the first inner shaft 102, the suspension portion 111M, and the sliding portion 110. By covering the suspension portion 111M, the suspension portion 111M is maintained so as to be forcibly closed. The outer sheath is disposed inside the hollow outer sheath shaft disposed instead of the first and second wire shafts 117a and 117b in the outer shaft 101. The outer sheath can be moved in the longitudinal direction of the catheter 100 between the outer peripheral face of the first inner shaft 102 and the inner peripheral face of the outer sheath shaft. The suspension portion 111M can be expanded by moving the outer sheath to the proximal end side of the suspension portion 111M.

For example, a configuration for detecting an impedance of the suspension portion 111 of the expansion/contraction portion 12 may be provided. The impedance of the suspension portion 111 changes depending on a degree of the contact between the suspension portion 111 and the living tissue. Thus, the degree of the contact between the suspension portion 111 and the living tissue can be derived from the detected impedance of the suspension portion 111. By adjusting the degree of expansion of the suspension portion 111 depending on the derived contact degree, the catheter 100 can be securely fixed and deviation of the catheter 100 can be further suppressed (in other words, the backup force of the catheter 100 can be securely obtained). Also, accumulation of the impedance data of the suspension portion 111 makes it possible to comprehend a structure and a condition of a tissue in contact with the suspension portion 111 to contribute to improvement of a success rate of the procedure.

Modification Example 5

The configurations of the catheters 100, 100A, 100B, 100R, 100T, and 100V in the first to eleventh aspects of the disclosed embodiments and the configurations of the catheters 100, 100A, 100B, 100R, 100T, and 100V of the modification examples 1 to 4 may be appropriately combined. For example, for the catheter having no second lumen 116 in the eleventh aspect of the disclosed embodiments, the expansion/contraction portions 12A to 12U explained in the second to tenth aspects of the disclosed embodiments may be adopted. For example, the expansion/contraction portions 12A to 12U explained in the second to tenth aspects of the disclosed embodiments can also be combined. For example, the rigidities may be made different between the central portion CP and the distal end and proximal end portions DP and PP in the suspension portion 111 by changing at least two of the thickness, the width, and the presence of the holes. For example, after at least two of the thickness, the width, and the presence of the holes are changed between the central portion CP and the distal end and proximal end portions DP and PP in the suspension portion 111, the cross-sectional shape of the suspension portion 111 may be bent in a protrusion shape.

As described above, the present aspects have been explained based on the embodiments and the modification examples, and the embodiments of the aforementioned aspects are intended to facilitate understanding of the present aspects and do not limit the present aspects. The present aspects can be modified and improved without departing from the gist of the aspects and claims, and the present aspects include equivalents thereof. In addition, if technical characteristics of the present aspects are not explained as essentials in this specification, the technical characteristics can be appropriately deleted.

What is claimed is:
1. A recanalization catheter system comprising:
  a catheter comprising:
    a shaft having:
      a first lumen inside the shaft;
      a second lumen extending from a proximal end toward a distal end of the shaft and that is juxtaposed with the first lumen and is shorter than the first lumen in a longitudinal direction of the shaft;
      a first opening allowing a side portion of the first lumen to communicate with an environment outside the catheter;
      a second opening allowing a distal end portion of the second lumen to communicate with the environment outside the catheter; and
      a tip opening allowing a distal end portion of the first lumen to communicate with the environment outside the catheter;
    a suspension portion attached to an outer peripheral face of the shaft;
  a sensor configured to be inserted into the first lumen and to acquire information on a living tissue in the environment outside the catheter; and
  a delivery guide wire configured to be inserted through the tip opening into the first lumen, then pulled out externally through the first opening, and then inserted through the second opening into the second lumen, wherein:
the first opening is located between the second opening and the tip opening in the longitudinal direction of the shaft, and
the suspension portion is made of a material that can be observed by the sensor.

2. The recanalization catheter system according to claim 1, further comprising:
a device configured to be inserted into the second lumen after removal of the delivery guide wire, be led to the environment outside the catheter through the second opening, and penetrate the living tissue,
wherein the material of the suspension portion has an acoustic impedance that is different from an acoustic impedance of the living tissue.

3. A recanalization catheter system comprising:
a catheter comprising:
a shaft having:
a first lumen inside the shaft;
a second lumen extending from a proximal end toward a distal end of the shaft and that is juxtaposed with the first lumen and is shorter than the first lumen in a longitudinal direction of the shaft;
a first opening allowing a side portion of the first lumen to communicate with an environment outside the catheter;
a second opening allowing a distal end portion of the second lumen to communicate with the environment outside the catheter; and
a tip opening allowing a distal end portion of the first lumen to communicate with the environment outside the catheter;
a sensor configured to be inserted into the first lumen and to acquire information on a living tissue in the environment outside the catheter; and
a delivery guide wire configured to be inserted through the tip opening into the first lumen, then pulled out externally through the first opening, and then inserted through the second opening into the second lumen,
wherein the first opening is located between the second opening and the tip opening in the longitudinal direction of the shaft.

* * * * *